United States Patent
Ryu et al.

(10) Patent No.: US 11,480,878 B2
(45) Date of Patent: Oct. 25, 2022

(54) MONOMERS, POLYMERS AND PHOTORESIST COMPOSITIONS

(71) Applicant: Rohm and Haas Electronic Materials Korea Ltd., Chungcheongnam-Do (KR)

(72) Inventors: Eui Hyun Ryu, Chungcheongnam-Do (KR); Min Kyung Jang, Chungcheongnam- do (KR); Jung Woo Kim, Chungcheongnam-Do (KR); Kwang-Mo Choi, Chungcheongnam-Do (KR); Hyun Jeon, Chungcheongnam-Do (KR); Woo-Hyung Lee, Chungcheongnam-Do (KR); Myung-Yeol Kim, Chungcheongnam-Do (KR)

(73) Assignee: ROHM AND HAAS ELECTRONIC MATERIALS KOREA LTD., Chungcheongnam-Do (KR)

( * ) Notice: Subject to any disclaimer, the term of this patent is extended or adjusted under 35 U.S.C. 154(b) by 0 days.

(21) Appl. No.: 15/253,845

(22) Filed: Aug. 31, 2016

(65) Prior Publication Data

US 2018/0059545 A1    Mar. 1, 2018

(51) Int. Cl.
| | |
|---|---|
| G03F 7/039 | (2006.01) |
| G03F 7/38 | (2006.01) |
| C08F 218/14 | (2006.01) |
| C08F 220/28 | (2006.01) |
| C07C 69/54 | (2006.01) |
| C07C 69/21 | (2006.01) |
| C07C 69/63 | (2006.01) |
| G03F 7/11 | (2006.01) |
| G03F 7/004 | (2006.01) |
| C07C 69/653 | (2006.01) |
| G03F 7/038 | (2006.01) |
| G03F 7/09 | (2006.01) |
| G03F 7/16 | (2006.01) |
| G03F 7/20 | (2006.01) |
| G03F 7/32 | (2006.01) |

(52) U.S. Cl.
CPC ............ *G03F 7/0392* (2013.01); *C07C 69/21* (2013.01); *C07C 69/54* (2013.01); *C07C 69/63* (2013.01); *C07C 69/653* (2013.01); *C08F 218/14* (2013.01); *G03F 7/0046* (2013.01); *G03F 7/038* (2013.01); *G03F 7/0397* (2013.01); *G03F 7/091* (2013.01); *G03F 7/11* (2013.01); *G03F 7/162* (2013.01); *G03F 7/168* (2013.01); *G03F 7/2041* (2013.01); *G03F 7/327* (2013.01); *G03F 7/38* (2013.01); *C08F 220/283* (2020.02)

(58) Field of Classification Search
CPC ... C08F 218/14; C08F 220/283; G03F 7/0392
See application file for complete search history.

(56) References Cited

U.S. PATENT DOCUMENTS

| | | |
|---|---|---|
| 5,843,624 A | 12/1998 | Houlihan et al. |
| 6,048,662 A | 4/2000 | Bruhnke et al. |
| 6,048,664 A | 4/2000 | Houlihan et al. |
| 6,057,083 A | 5/2000 | Taylor et al. |
| 6,136,501 A | 10/2000 | Trefonas, III et al. |
| 6,306,554 B1 | 10/2001 | Barclay et al. |
| 6,680,159 B2 | 1/2004 | Barclay et al. |
| 6,692,888 B1 | 2/2004 | Barclay et al. |
| 7,244,542 B2 | 7/2007 | Bae et al. |
| 7,968,268 B2 | 6/2011 | Wang |
| 8,206,886 B2 | 6/2012 | Kodama |
| 8,257,902 B2 | 9/2012 | Wang et al. |
| 2011/0255069 A1 | 10/2011 | Wang |
| 2012/0064456 A1 | 3/2012 | Bae et al. |
| 2012/0171626 A1* | 7/2012 | Wang ................. G03F 7/0046 430/325 |
| 2016/0052859 A1* | 2/2016 | Ochiai ................ C08F 122/18 430/270.1 |

FOREIGN PATENT DOCUMENTS

| | | |
|---|---|---|
| EP | 0930542 A1 | 7/1999 |
| EP | 1008913 A1 | 6/2000 |
| WO | 0186353 A1 | 11/2001 |

\* cited by examiner

*Primary Examiner* — John S Chu
(74) *Attorney, Agent, or Firm* — Cantor Colburn LLP

(57) ABSTRACT

In one preferred embodiment, polymers are provided that comprise a structure of the following Formula (I):

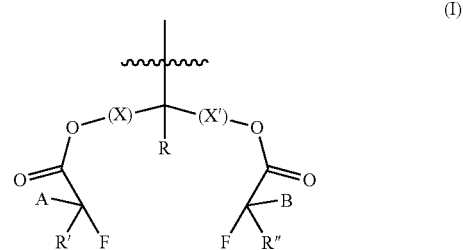

(I)

Photoresists that comprises such polymers also are provided.

18 Claims, No Drawings

MONOMERS, POLYMERS AND PHOTORESIST COMPOSITIONS

BACKGROUND

The invention relates generally to the manufacture of electronic devices. More specifically, this invention relates to photoresist compositions and to photolithographic processes which allow for the formation of fine patterns using a negative tone development process.

Photoresists are photosensitive films used for the transfer of images to a substrate. A coating layer of a photoresist is formed on a substrate and the photoresist layer is then exposed through a photomask to a source of activating radiation. Following exposure, the photoresist is developed to provide a relief image that permits selective processing of a substrate.

Considerable effort has been made to extend the practical resolution capabilities of photoresist compositions, including though immersion lithography. In immersion lithography, the numerical aperture of the exposure tool lens is increased through use of a fluid to focus more light into the resist film. More particularly, immersion lithography utilizes a relatively high refractive index fluid between the last surface of an imaging device (e.g. ArF stepper) and the first on a wafer or other substrate. See in US20120171626A1; U.S. Pat. No. 7,968,268B2; US20110255069A1 KR1141229B1; KR2006114293A1; KR2009028739A1; KR2009046730A1; and KR2011053407A1.

Electronic device manufacturers continually seek increased resolution of a patterned photoresist image. It would be desirable to have new photoresist compositions that could provide enhanced imaging capabilities.

SUMMARY

We now provide new polymers and photoresists that comprise such polymers.

In one preferred embodiment, polymers are provided that comprise a structure of the following Formula (I):

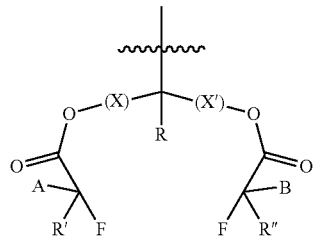

(I)

wherein in Formula (I):

X and X' are the same or different linker;

R is hydrogen or a non-hydrogen substituent;

A and B are each independently hydrogen or flourine;

R' and R" are each independently hydrogen or a non-hydrogen substituent, with at least one of R' and R" being a non-hydrogen substituent other than a halogen or a halogen-substituted group when R is hydrogen.

In a further embodiment, polymers are provided that comprise a structure of the following Formula (IIA):

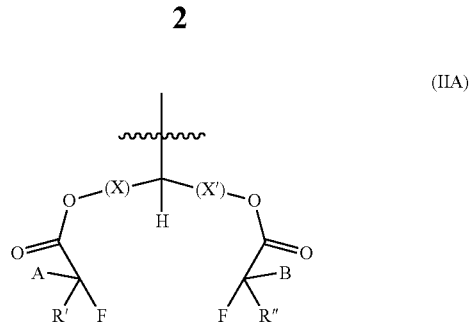

(IIA)

wherein in Formula (IIA):

X and X' are the same or different linker;

A and B are each independently hydrogen or fluorine; and

R' and R" are each independently hydrogen or a non-hydrogen substituent, with at least one of R' and R" being a non-hydrogen substituent other than a halogen or a halogen-substituted group when R is hydrogen.

In certain preferred polymers of Formula (I) or (IIA), R' and R" are each independently hydrogen, non-halogenated alkyl suitably having 1 to 12 carbon atoms, halogenated alkyl suitably having 1 to 12 carbon atoms including fluorinated alkyl such as —$CF_3$, or heteroalkyl suitably having 1 to 12 carbon atoms such as alkoxy. In additional certain preferred polymers of Formula (I), R is hydrogen or optionally substituted alkyl or alkoxy suitably having 1 to 6 carbons. In additional certain preferred polymers of Formula (I) or (IIA), X and X' are different, or in other preferred polymers X and X' may be the same. In various preferred polymers of Formulae (I) or (IIA), at least one or both X and X' is a chemical bond or —$CH_2$—. X and X' suitably may be a chemical bond or contain one or more carbon atoms, typically 1 to about 4, 5, 6, 7, 8, 9 or 10 carbon atoms and may comprise an alkyl group, ether group, ester group, amide group, or sulfonate group.

In a yet further embodiment, polymers are provided that comprise a structure of the following Formula (IIB):

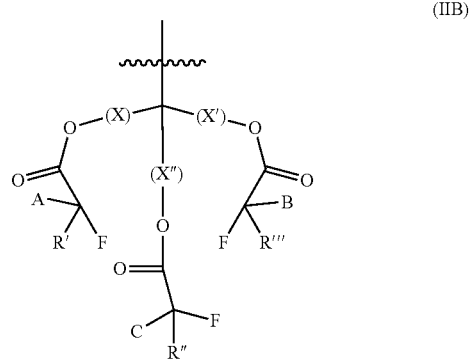

(IIB)

wherein in Formula (IIB):

X, X' and X" are each the same or different linker;

A, B and C are each independently hydrogen or fluorine; and

R', R" and R'" are each independently hydrogen or a non-hydrogen substituent.

In certain preferred polymers of Formula (IIB), R', R" and R'" are each independently hydrogen, non-halogenated alkyl suitably having 1 to 12 carbon atoms, halogenated alkyl suitably having 1 to 12 carbon atoms including fluorinated alkyl such as —CF$_3$, or heteroalkyl suitably having 1 to 12 carbon atoms such as alkoxy. In additional certain preferred polymers of Formula (IIB), at least two of X, X' and X" are different, or in other preferred polymers at least two of X, X' and X" may be the same. In various preferred polymers of Formula (IIB), at least one, two or each of X, X' and X" is a chemical bond or —CH$_2$—. X, X' and X" suitably may be a chemical bond or contain one or more carbon atoms, typically 1 to about 4, 5, 6, 7, 8, 9 or 10 carbon atoms and may comprise an alkyl group, ether group, ester group, amide group, or sulfonate group.

In Formulae (I), (IIA) and (IIB), the depicted wavy line at the top of the formulae structures depicts a chemical bond such as attachment to a group that links to a polymer backbone, or the wavy line depicts a chemical bond or chemical linkage (e.g. —CH$_2$—)s that is part of the polymer backbone.

Polymers of the invention may comprise multiple distinct repeat units. Thus, the present polymers may be homopolymers, or more typically will be copolymer, terpolymer, tetrapolymer, pentapolymer or other higher order polymer with 2, 3, 4, 5 or more distinct repeat units. Such additional repeat units need not comprise a structure of the above Formulae (I), (IIA) or (IIB), provided at least one unit of the polymer comprises a structure of the above Formulae (I), (IIA) or (IIB). The examples below depict preferred additional polymer units.

Particularly preferred polymers of the invention may comprise polymerized acrylate units. In a related embodiment, preferred polymers include those that polymer comprise units obtained by polymerization of one or more monomers of the following Formula (III):

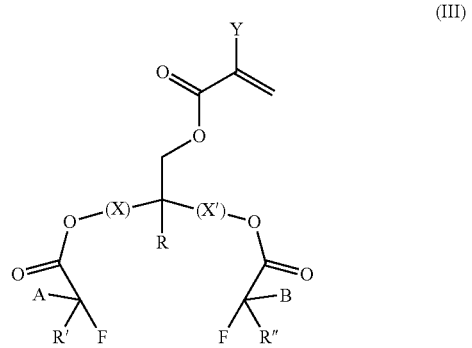

(III)

wherein in Formula (III):
Y is hydrogen or optionally substituted alkyl;
X and X' are the same or different linker;
R is hydrogen or a non-hydrogen substituent;
A and B are each independently hydrogen or fluorine; and
R' and R" are each independently hydrogen or a non-hydrogen substituent,
with at least one of R' and R" being a non-hydrogen substituent other than a halogen or a halogen-substituted group when R is hydrogen. In Formula (III), Y is suitably hydrogen or optionally substituted C$_{1-3}$alkyl including optionally substituted methyl. In certain preferred monomers of Formula (III), R is hydrogen or optionally substituted alkyl or alkoxy suitably having 1 to 6 carbons. In certain preferred monomers of Formula (III), R' and R" are each independently hydrogen, non-halogenated alkyl suitably having 1 to 12 carbon atoms, halogenated alkyl suitably having 1 to 12 carbon atoms including fluorinated alkyl such as —CF$_3$, or heteroalkyl suitably having 1 to 12 carbon atoms such as alkoxy. In additional certain preferred monomers of Formula (III), X and X' are different, or in other preferred monomers X and X' may be the same. In various preferred monomers of Formula (III), at least one or both of X and X' is a chemical bond or —CH$_2$—. X and X' suitably may be a chemical bond or contain one or more carbon atoms, typically 1, 2, 3, 4, 5, 6, 7, 8, 9 or 10 carbon atoms and may comprise an alkyl group, ether group, ester group, amide group, or sulfonate group.

Preferred polymers include those where at least one or both of A and B (Formulae I, IIA, IIB, III) is fluorine or fluoroalkyl (e.g. a group that has one or preferably more fluorine atoms and 1 to 20 carbon atoms) or at least one, two or each of A', B' and C' (Formula (IIB) is fluorine or (e.g. a group that has one or preferably more fluorine atoms and 1 to 20 carbon atoms).

Photoresists are also provided that comprise one or more acid generators and one or more polymers as disclosed herein, including a polymer comprising a structure of any of the Formulae (I), (IIA) or (IIB) as disclosed above. In preferred aspects, a photoresist of the invention may comprise a second polymer distinct from a polymer of any of the Formulae (I), (IIA) or (IIB). A polymer comprising a structure of any one of Formula (I), (IIA) or (IIB) is some referred to herein as a "first polymer" of a photoresist composition. In certain preferred aspects, the present photoresists may comprise an additional polymer (sometimes referenced to herein as a "second polymer" of the photoresist composition) which is distinct from the first polymer. The second polymer optionally may comprise acid-labile groups. As further discussed below, in certain embodiments, the first and second polymers may have differing surface energies.

In certain preferred aspects, the first polymer may further comprise third units that (1) comprise one or more hydrophobic groups and (2) are repeat units that comprise a structure of Formulae (I), (IIA) or (IIB). Suitably, such one or more hydrophobic groups each comprise 3, 4, 5, 6, 7, 8 or more carbon atoms such as optionally substituted alkyl or alkoxy groups that have such number of carbon atoms.

Methods of processing a photoresist composition are also provided that may suitably comprise applying a layer of a photoresist composition as disclosed herein on a substrate; exposing the photoresist composition layer to activating radiation; and developing the exposed photoresist composition to provide a photoresist relief image. Suitably, the photoresist composition layer may be immersion exposed. Dry (non-immersion) exposure also will be suitable. In certain aspects, implant and EUV lithography processes are also preferred.

In a preferred aspect, unexposed portions of the photoresist layer are removed by the developer, leaving a photoresist pattern over the one or more layer to be patterned. The patternwise exposing can be conducted by immersion lithography or, alternatively, using dry exposure techniques.

According to a further aspect, coated substrates are provided. The coated substrates comprise a substrate and a layer of a photoresist composition of the invention over a surface of the substrate.

Electronic devices formed by the disclosed methods are also provided, including devices formed by the disclosed negative tone development processes.

Monomers are also provided that comprises a structure of any one of Formulae (I), (IIA), (IIB) or (III) as disclosed above as well as any of Formulae](A) through (F) below.

As used herein, the articles "a" and "an" are inclusive of one or more unless otherwise indicated expressly or by context.

Other aspects of the invention are disclosed infra.

DETAILED DESCRIPTION

As discussed, in certain preferred aspects, a photoresist of the invention may comprise at least two distinct polymers: 1) a first polymer that comprises a structure of Formula (I), (IIA) or (IIB) and 2) a second polymer that is distinct from the first polymer. The second polymer need not contain a structure of formulae (I), (IIA) or (IIB). In preferred compositions, the first polymer can migrate toward the upper surface of the resist coating layer during coating of the photoresist composition. In certain systems, this can form a surface layer substantially made up of the first polymer. Following exposure and post exposure bake (PEB), the resist coating layer can be developed, including in a developer comprising an organic solvent. If an organic developer is employed, such developer removes unexposed regions of the photoresist layer and the surface layer of the exposed regions. Aqueous alkaline developer also can be utilized that remove exposed regions of a resist coating layer. Benefits of the inventive photoresist compositions can be achieved when using the compositions in dry lithography or immersion lithography processes. When used in immersion lithography, preferred photoresist compositions can further exhibit reduced migration (leaching) of photoresist materials into an immersion fluid also a result of the additive polymer's migration to the resist surface. Significantly, this can be achieved without use of a topcoat layer over the photoresist.

As discussed above, various materials and substituents (including groups of Formulae (I), (IIA), (IIB) and (III) above) that are "optionally substituted" may be suitably substituted at one or more available positions by e.g. halogen (F, Cl, Br, I); nitro; hydroxy; amino; alkyl such as $C_{1-8}$ alkyl; alkenyl such as $C_{2-8}$ alkenyl; alkylamino such as $C_{1-8}$ alkylamino; carbocyclic aryl such as phenyl, naphthyl, anthracenyl, etc; and the like.

As referred to herein, suitable heteroalkyl include optionally substituted C1-20alkoxy, optionally substituted alkylthio preferably having 1 to about 20 carbon atoms; optionally substituted alkylsulfinyl preferably 1 to about 20 carbon atoms; optionally substituted alkylsulfonyl preferably having 1 to about 20 carbon atoms; and optionally substituted alkylamine preferably having 1 to about 20 carbon atoms.

The photoresists can be used at a variety of radiation wavelengths, for example, wavelengths of sub-400 nm, sub-300 or sub-200 nm, or with 248 nm, 193 nm and EUV (e.g., 13.5 nm) exposure wavelengths being preferred. The compositions can further be used in electron beam (E-beam) exposure processes. The photoresist compositions of the invention are preferably chemically-amplified materials.

As discussed, the first or additive polymers useful in the photoresist compositions comprise a structure of the above Formulae (I), (IIA) or (IIB). Such polymers may be prepared by polymerization of one or more monomers of the following structures:

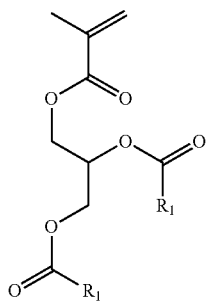

(A)

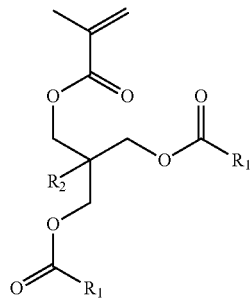

(B)

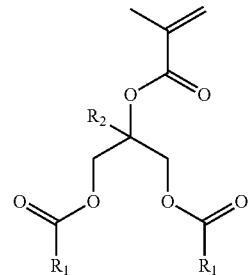

(C)

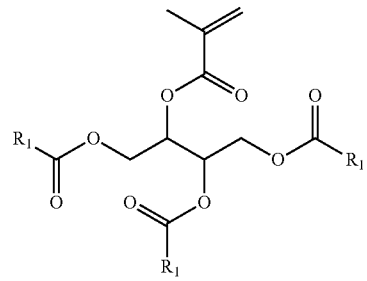

(D)

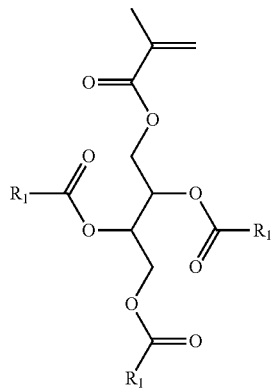

(E)

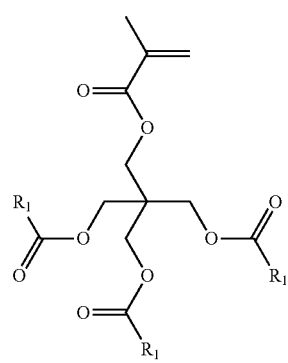

(F)

wherein in each of the above Formulae (A), (B), (C), (D), (E) and (F) each $R_1$ is independently a non-hydrogen substituent, such as optionally substituted alkyl for example $C_{1-20}$ alkyl more typically $C_{3-16}$ alkyl, including halogen-substituted $C_{3-16}$ alkyl particularly fluoro-substituted $C_{3-16}$ alkyl; and $R_2$ is a non-hydrogen substituted such as optionally substituted alkyl including unsubstituted $C_{1-12}$ alkyl particularly unsubstituted alkyl having 1, 2, 3, 4 or 5 carbon atoms.

Exemplary preferred monomers of Formula (A) above include the following:

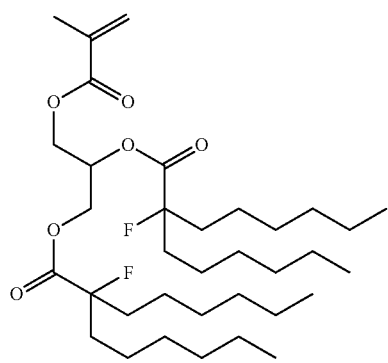

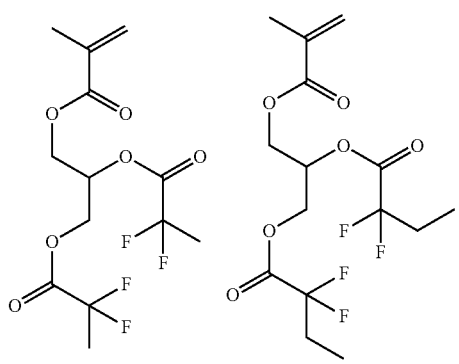

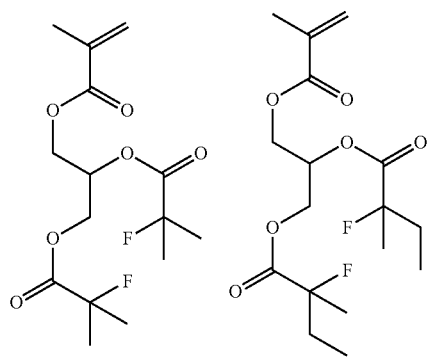

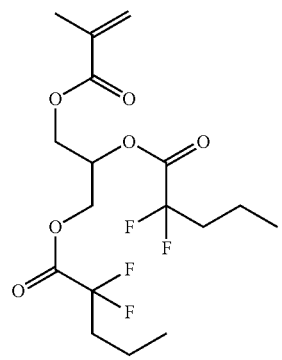

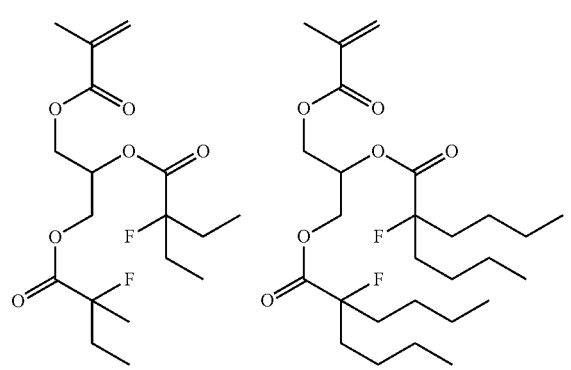

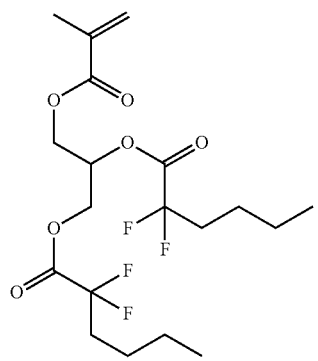

-continued
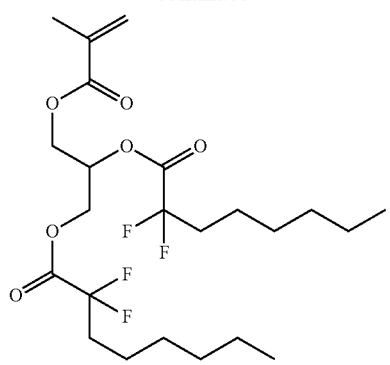
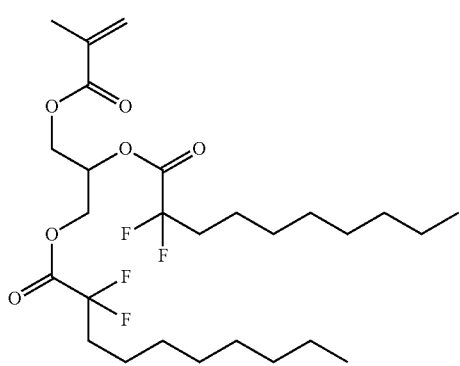
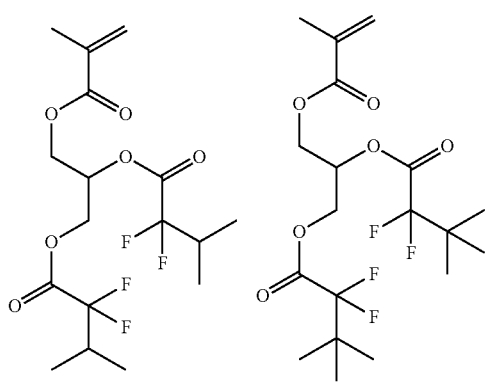
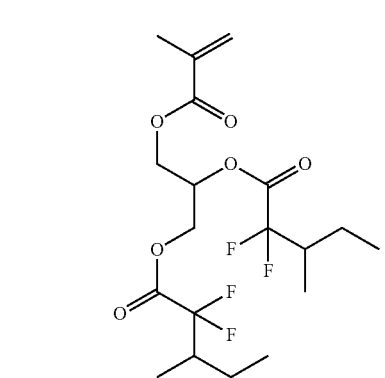
-continued
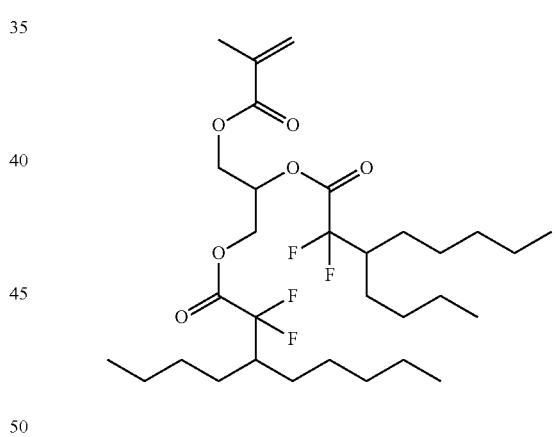
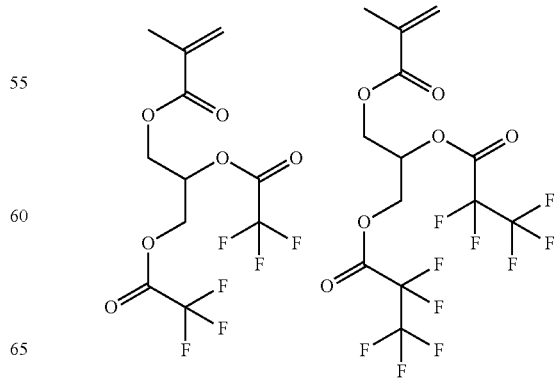

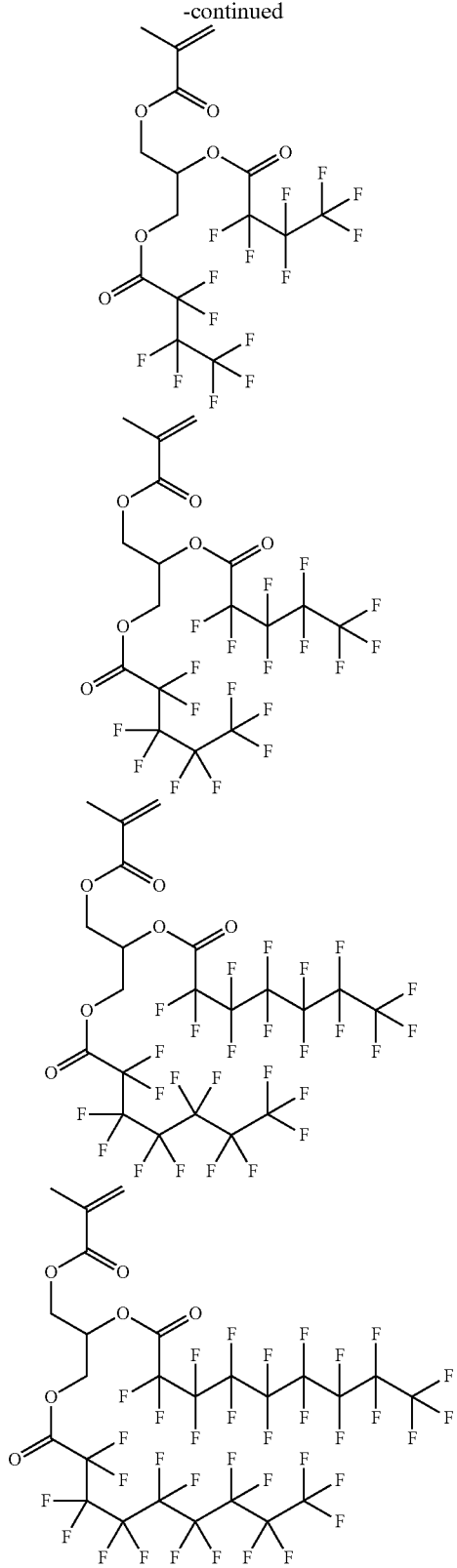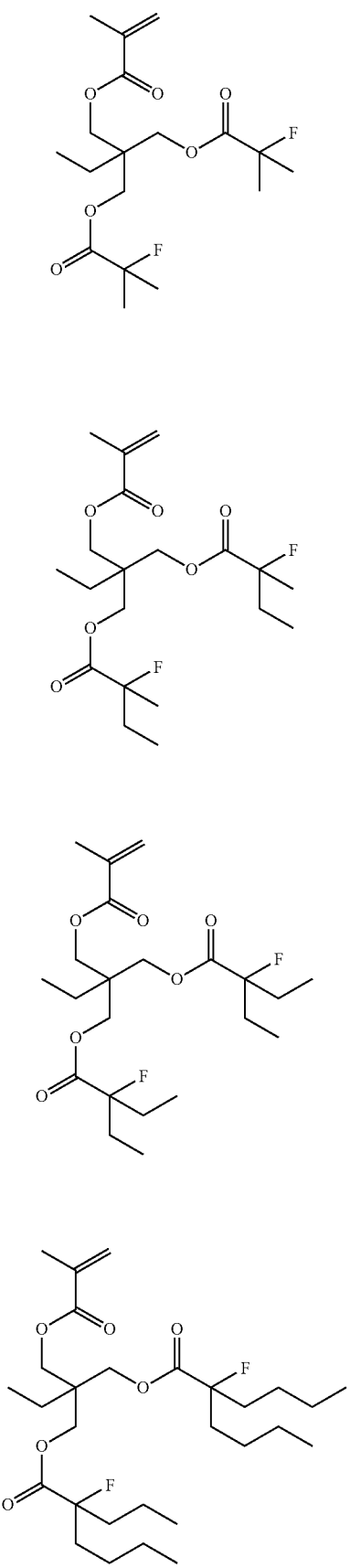
Exemplary preferred monomers of Formula (B) above include the following:

13
-continued
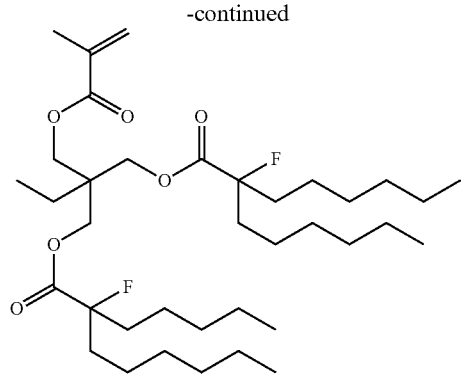
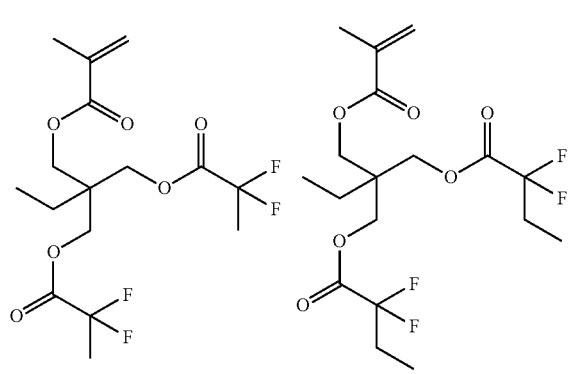
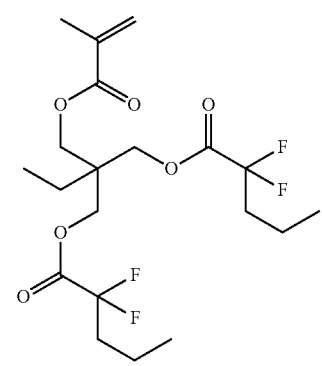
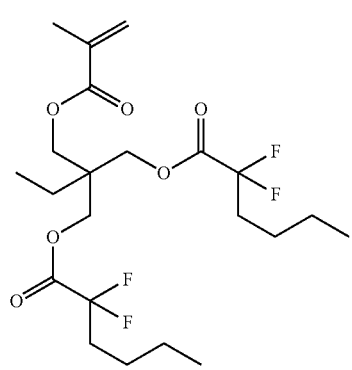
14
-continued
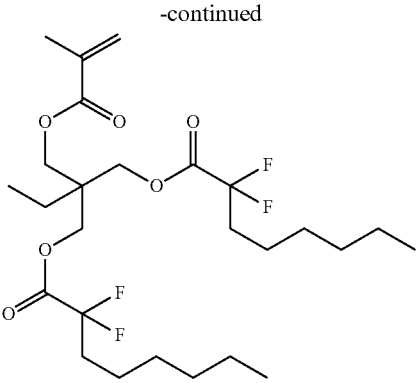
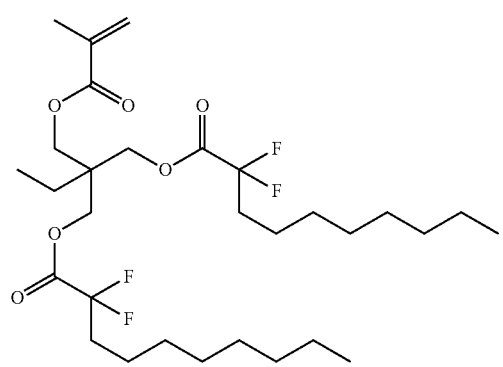
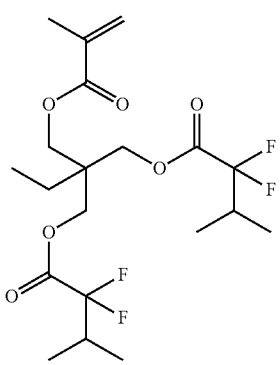
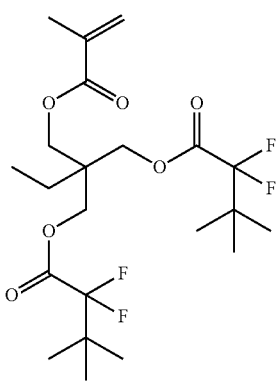

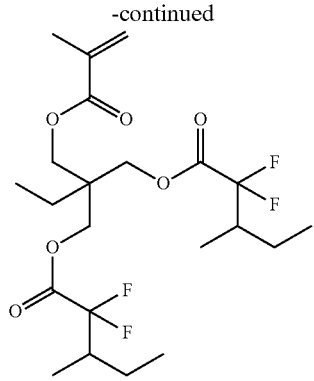
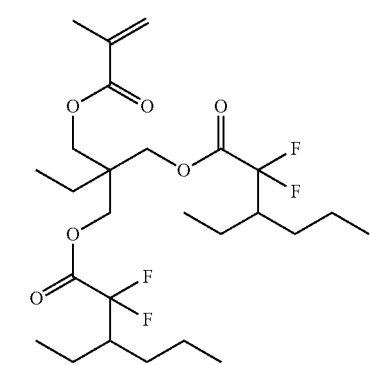
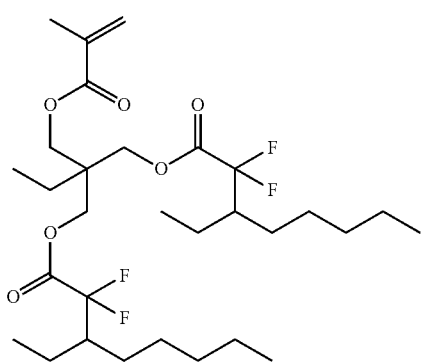
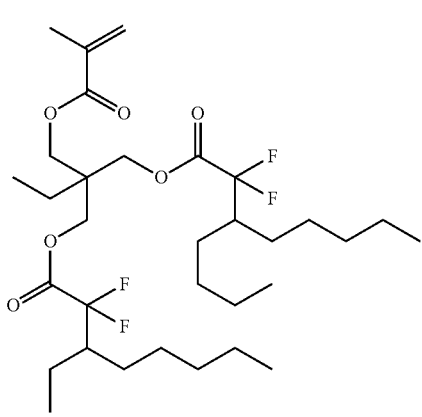
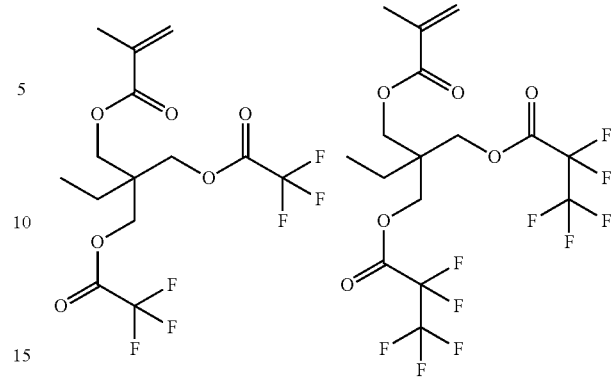
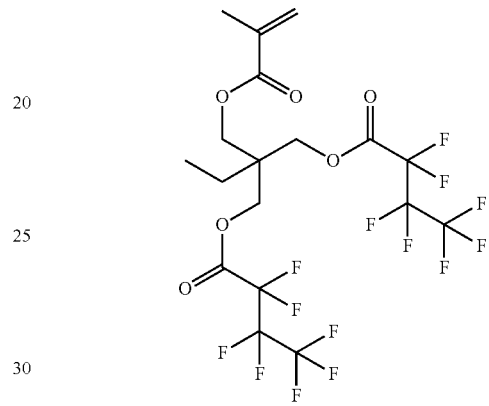
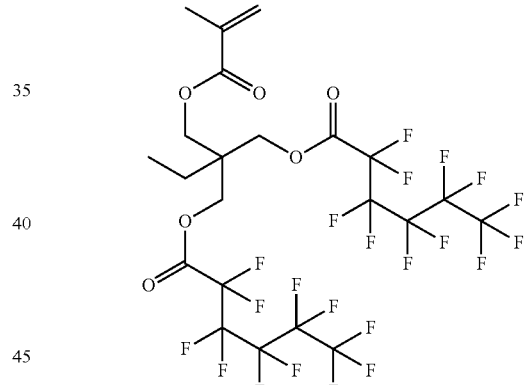
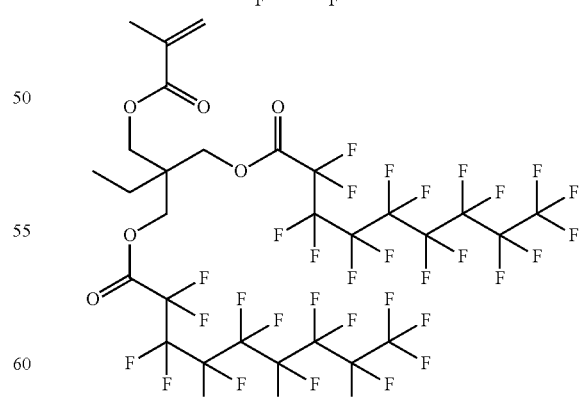
Exemplary preferred monomers of Formula (D) above include the following:

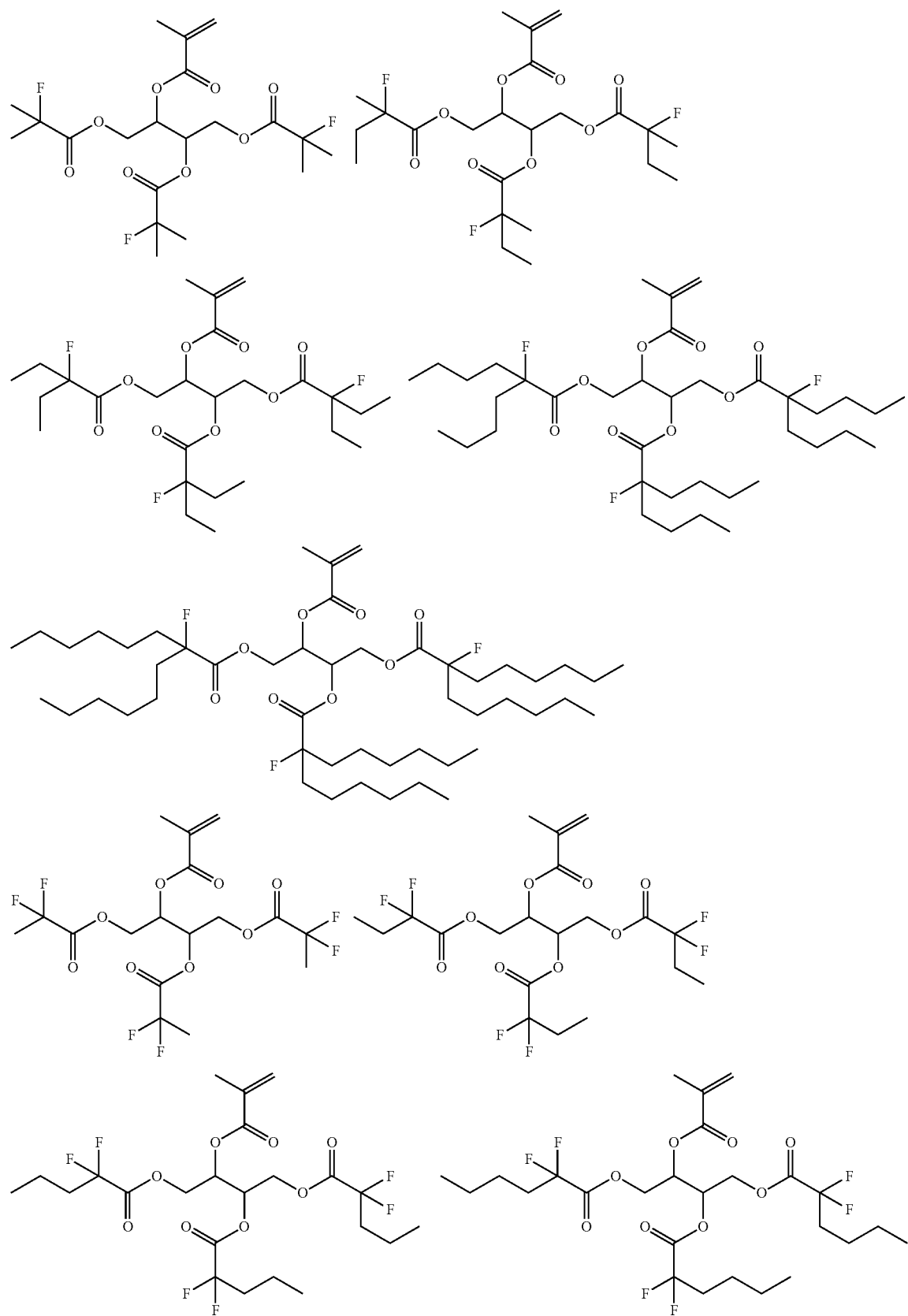

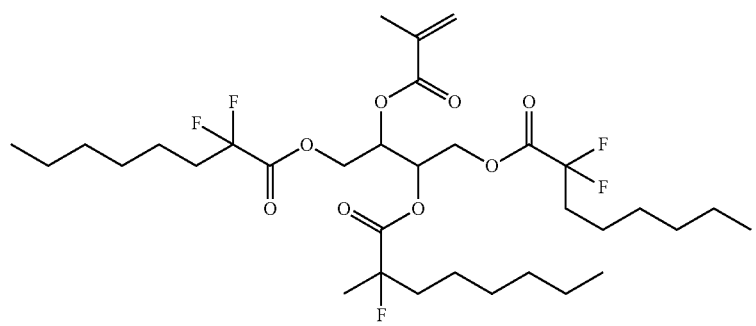
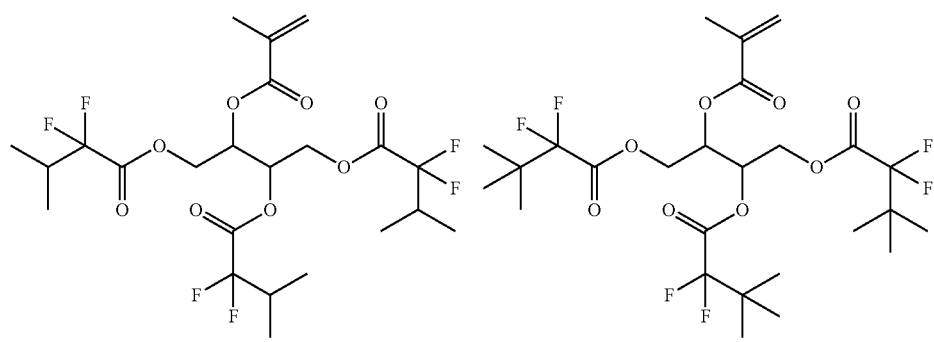
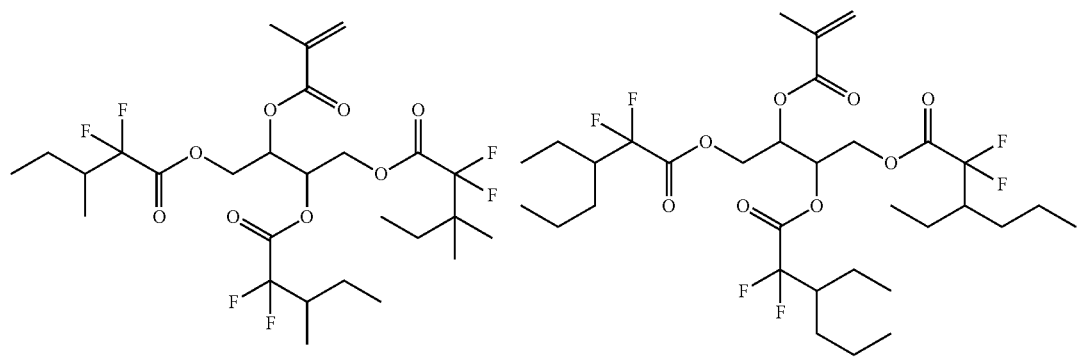
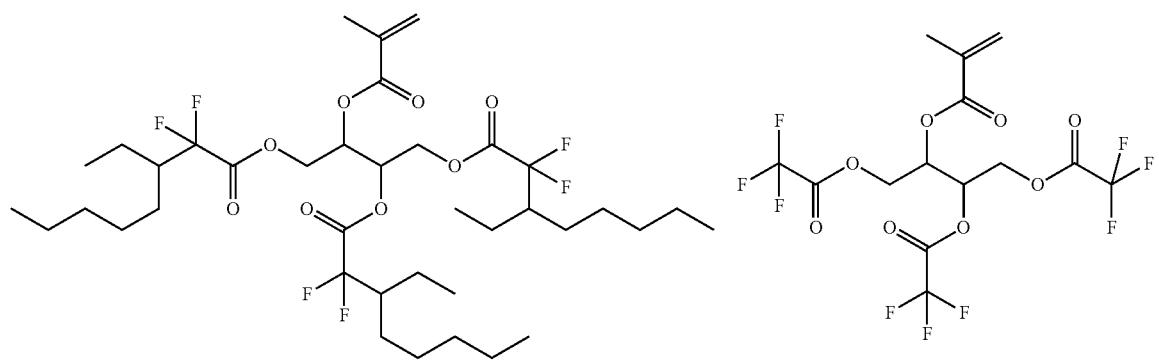

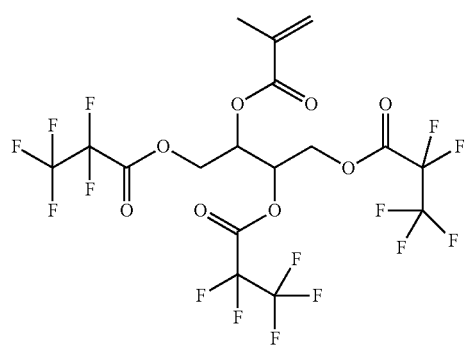
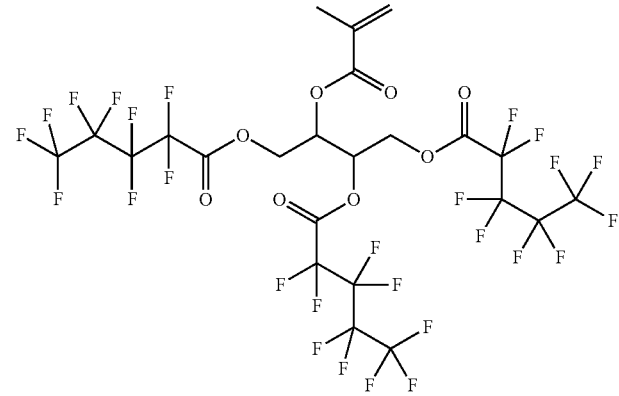
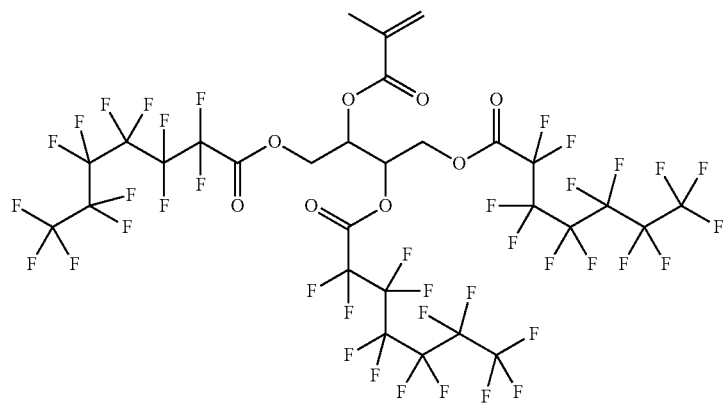

Compounds of the above Formulae (A), (B), (C), (D), (E), (F) and (III) can be readily prepared. For instance, a polyhydroxy acrylate or methacrylate compound can be acylated under basic conditions. A polyhydroxy acrylate or methacrylate compound can be reacted with an optionally substituted alkylcarboxy compound, including a halogenated, particularly fluorinated alkylcarboxy compound. See, for instance, Examples 1-6 which follow.

Polymers that comprise a structure of Formula (I), (IIA) or (IIB) also can be readily prepared. For instance, a polymerizable compound the above Formulae (A), (B), (C), (D), (E) and (F) can be reacted to provide a homopolymer, or reacted with other distinct compounds to provide a higher order polymer such as a copolymer (at least two distinct repeat units), terpolymer(three distinct repeat units), tetrapolymer(four distinct repeat units), or pentapolymer (five distinct repeat units). See Examples 7-12 which follow for exemplary preferred syntheses.

Optional Second Polymers of Photoresists

In preferred embodiments, the photoresist compositions comprise one or more second or matrix polymers (distinct from the first polymer) that comprise an acid labile group. The acid labile group is a chemical moiety that readily undergoes deprotection reaction in the presence of an acid. The second or matrix polymer as part of a layer of the photoresist composition undergoes a change in solubility in a developer described herein as a result of reaction with acid generated from the photoacid and/or thermal acid generator during lithographic processing, particularly following softbake, exposure to activating radiation and post exposure bake. This results from photoacid-induced cleavage of the acid labile group, causing a change in polarity of the second polymer. The acid labile group can be chosen, for example, from tertiary alkyl carbonates, tertiary alkyl esters, tertiary alkyl ethers, acetals and ketals. Preferably, the acid labile group is an ester group that contains a tertiary non-cyclic alkyl carbon or a tertiary alicyclic carbon covalently linked to a carboxyl oxygen of an ester of the second matrix polymer. The cleavage of such acid labile groups results in the formation of carboxylic acid groups. Suitable acid labile-group containing units include, for example, acid-labile (alkyl)acrylate units, such as t-butyl (meth)acrylate, 1-methylcyclopentyl (meth)acrylate, 1-ethylcyclopentyl (meth)acrylate, 1-isopropylcyclopentyl (meth)acrylate, 1-propylcyclopentyl (meth)acrylate, 1-methylcyclohexyl (meth)acrylate, 1-ethylcyclohexyl (meth)acrylate, 1-isopropylcyclohexyl (meth)acrylate, 1-propylcyclohexyl (meth)acrylate, t-butyl methyladamantyl(meth)acrylate, ethylfenchyl(meth)acrylate, and the like, and other cyclic, including alicyclic, and non-cyclic (alkyl) acrylates. Acetal and ketal acid labile groups can be substituted for the hydrogen atom at the terminal of an alkali-soluble group such as a carboxyl group or hydroxyl group, so as to be bonded with an oxygen atom. When acid is generated, the acid cleaves the bond between the acetal or ketal group and the oxygen atom to which the acetal-type acid-dissociable, dissolution-inhibiting group is bonded. Exemplary such acid labile groups are described, for example, in U.S. Pat. Nos. 6,057,083, 6,136,501 and 8,206,886 and European Pat. Pub. Nos. EP01008913A1 and EP00930542A1. Also suitable are acetal and ketal groups as part of sugar derivative structures, the cleavage of which would result in the formation of hydroxyl groups, for example, those described in U.S. Patent Application No. US2012/0064456A1.

For imaging at certain sub-200 nm wavelengths such as 193 nm, the second or matrix polymer is typically substantially free (e.g., less than 15 mole %), preferably completely free, of phenyl, benzyl or other aromatic groups where such groups are highly absorbing of the radiation. Suitable polymers that are substantially or completely free of aromatic groups are disclosed in European Patent Publication No. EP930542A1 and U.S. Pat. Nos. 6,692,888 and 6,680,159.

Other suitable second or matrix polymers include, for example, those which contain polymerized units of a non-aromatic cyclic olefin (endocyclic double bond) such as an optionally substituted norbornene, for example, polymers described in U.S. Pat. Nos. 5,843,624 and 6,048,664. Still other suitable matrix polymers include polymers that contain polymerized anhydride units, particularly polymerized maleic anhydride and/or itaconic anhydride units, such as disclosed in European Published Application EP01008913A1 and U.S. Pat. No. 6,048,662.

Also suitable as the second or matrix polymer is a resin that contains repeat units that contain a hetero atom, particularly oxygen and/or sulfur (but other than an anhydride, i.e., the unit does not contain a keto ring atom). The heteroalicyclic unit can be fused to the polymer backbone, and can comprise a fused carbon alicyclic unit such as provided by polymerization of a norbornene group and/or an anhydride unit such as provided by polymerization of a maleic anhydride or itaconic anhydride. Such polymers are disclosed in International Pub. No. WO0186353A1 and U.S. Pat. No. 6,306,554. Other suitable hetero-atom group containing matrix polymers include polymers that contain polymerized carbocyclic aryl units substituted with one or more hetero-atom (e.g., oxygen or sulfur) containing groups, for example, hydroxy naphthyl groups, such as disclosed in U.S. Pat. No. 7,244,542.

In the case of sub-200 nm wavelengths such as 193 nm and EUV (e.g., 13.5 nm), the second or matrix polymer may include a unit containing a lactone moiety for controlling the dissolution rate of the second matrix polymer and photoresist composition. Suitable monomers for use in the second or matrix polymer containing a lactone moiety include, for example, the following:

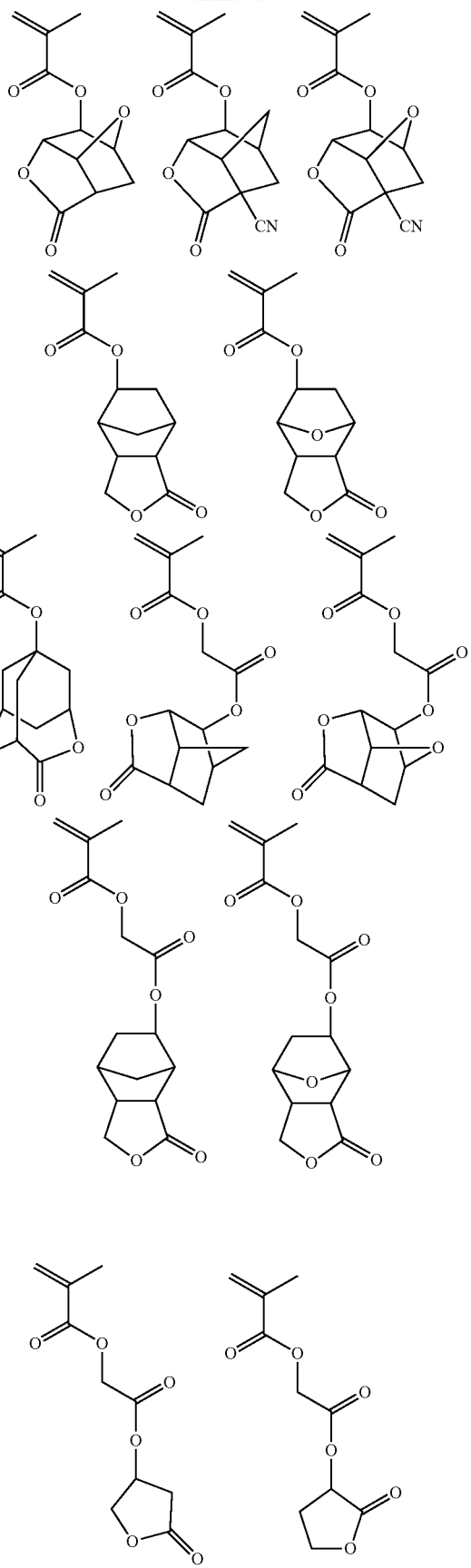

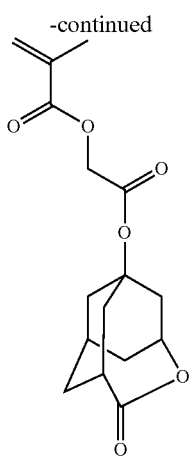

Such a second or matrix polymer further typically includes a unit containing a polar group, which enhances etch resistance of the matrix polymer and photoresist composition and provides additional means to control the dissolution rate of the matrix polymer and photoresist composition. Monomers for forming such a unit include, for example, the following:

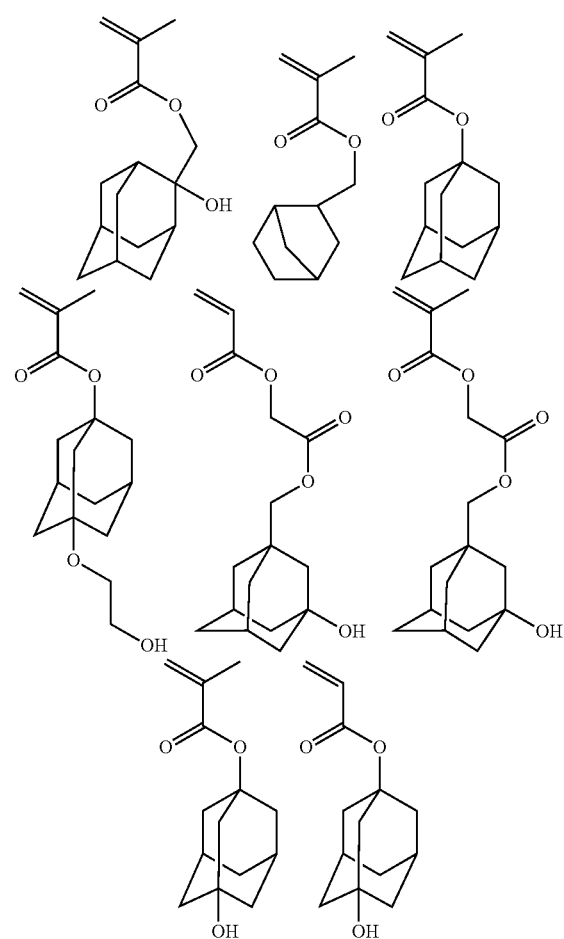

The second or matrix polymer can include one or more additional units of the types described above. Typically, the additional units for the second or matrix polymer will include the same or similar polymerizable group as those used for the monomers used to form the other units of the polymer, but may include other, different polymerizable groups in the same polymer backbone.

In preferred aspects, the second or matrix polymer has a higher surface energy than that of the first or additive polymer, described below, and should be substantially non-miscible with the second polymer. As a result of the difference in surface energies, segregation of the second polymer from the first polymer can take place during spin-coating. A suitable surface energy of the second or matrix polymer is typically from 20 to 50 mN/m, preferably from 30 to 40 mN/m.

While not to be limited thereto, exemplary second or matrix polymers include, for example, the following:

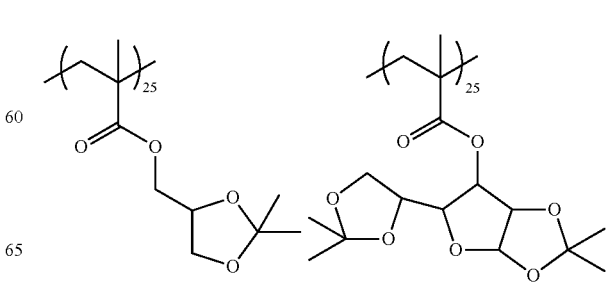

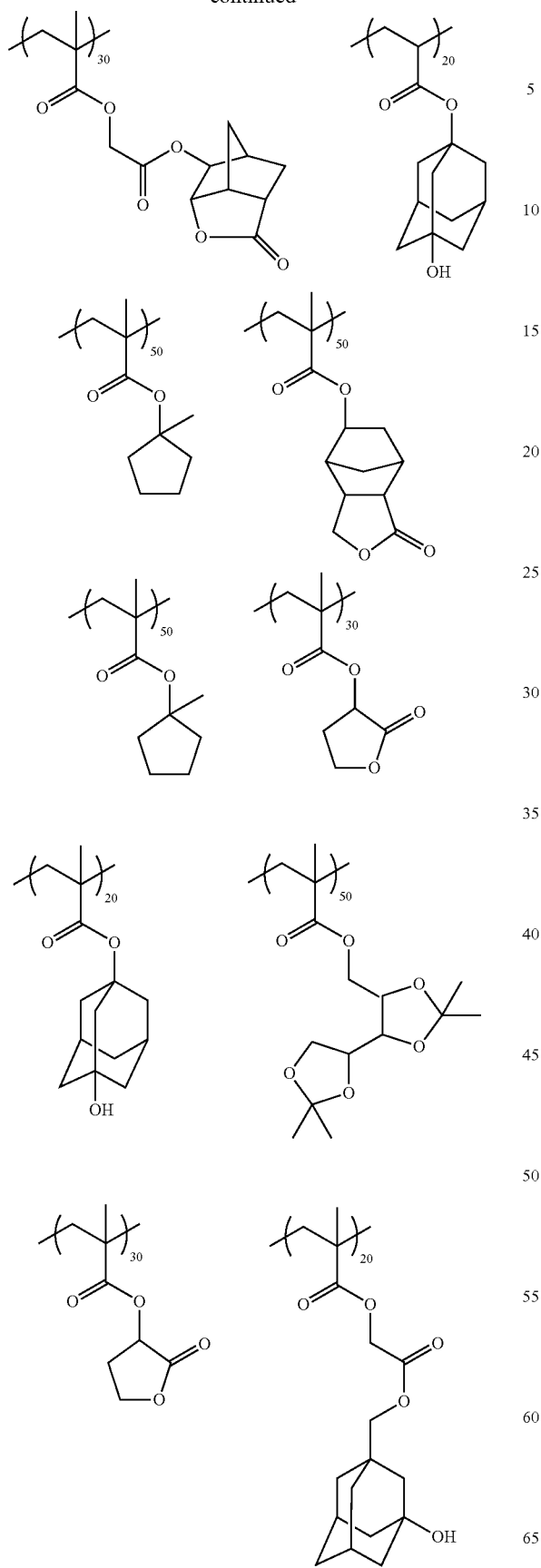
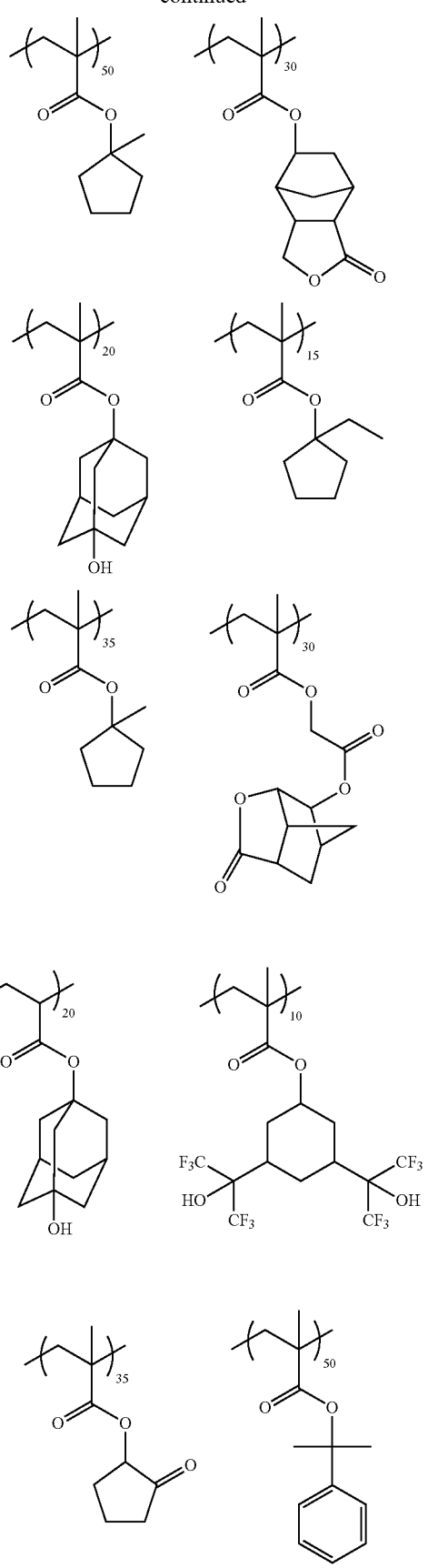

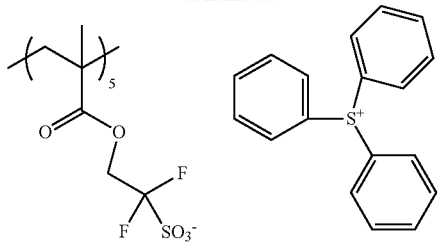

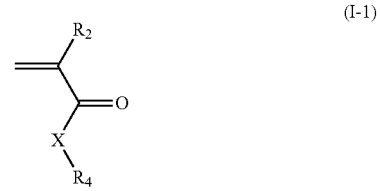

Suitable second or matrix polymers for use in the photoresist compositions of the invention are commercially available and can readily be made by persons skilled in the art. The second polymer is present in the resist composition in an amount sufficient to render an exposed coating layer of the resist developable in a suitable developer solution. Typically, the second polymer is present in the composition in an amount of from 50 to 95 wt % based on total solids of the resist composition. The weight average molecular weight $M_w$ of the second polymer is typically less than 100,000, for example, from 3000 to 100,000, more typically from 3000 to 15,000. Blends of two or more of the above-described second polymers can suitably be used in the photoresist compositions of the invention.

The first polymer that comprises a structure of Formula (I), (IIA or IIB) is preferably a material that has a lower surface energy than that of the second polymer and preferably is substantially non-miscible with the second polymer. In this way, segregation or migration of the first polymer to the top or upper portions of an applied photoresist layer during the coating process is facilitated. While the desired surface energy of the first polymer will depend on the particular second polymer and its surface energy, the first polymer surface energy is typically from 18 to 40 mN/m, preferably from 20 to 35 mN/m and more preferably from 29 to 33 mN/m. While the first polymer migrates to the upper surface of the resist layer during the coating process, it is preferable that there be some intermixing between the first polymer and second or matrix polymer immediately beneath the resist layer surface. Such intermixing is believed to aid in reducing surface inhibition in the resist layer by reduction or elimination of the acid generated in dark regions in the vicinity of the second or matrix polymer due to stray light. The extent of intermixing will depend, for example, on the difference in surface energy (SE) between the second or matrix polymer (MP) and first or additive polymer (AP) ($\Delta SE = SE_{MP} - SE_{AP}$). For given first or matrix and second or additive polymers, the degree of intermixing can be increased with reduced $\Delta SE$. The $\Delta SE$ is typically from 2 to 32 mN/m, preferably from 5 to 15 mN/m.

The first polymer that comprises a structure of Formula (I), (IIA or IIB) is preferably free of silicon. Silicon-containing polymers exhibit a significantly lower etch rate than organic photoresist polymers in certain etchants. As a result, aggregation of a silicon-containing first polymer at the surface of an organic second polymer-based resist layer can cause cone defects during the etching process. The first polymer may contain fluorine or can be free of fluorine. Preferred first polymers are soluble in the same organic solvent(s) used to formulate the photoresist composition. Preferred first polymers also will be soluble or become soluble upon post exposure bake (e.g., 120° C. for 60 seconds) in organic developers used in negative tone development processes.

As discussed, suitable first polymers that comprise a structure of Formula (I), (IIA) or (IIB) may contain one or more additional distinct units such as formed from monomers corresponding to the following general formula (I-1):

(I-1)

wherein: $R_2$ is chosen from hydrogen, fluorine and fluorinated and non-fluorinated C1 to C3 alkyl; and X is oxygen or sulfur; and $R_4$ is chosen from substituted and unsubstituted C1 to C20 linear, branched and cyclic hydrocarbons, preferably fluorinated and non-fluorinated C1 to C15 alkyl, more preferably fluorinated and non-fluorinated C3 to C8 alkyl and most preferably fluorinated and non-fluorinated C4 to C5 alkyl, with $R_4$ preferably being branched to provide a higher water receding contact angle when used in immersion lithography, and $R_4$ substitutions of haloalkyl and haloalcohol such as fluoroalkyl and fluoroalcohol being suitable.

As discussed, various moieties of monomers, polymers and other materials may be optionally substituted (or stated to be "substituted or unsubstituted"). A "substituted" substituent may be substituted at one or more available positions, typically 1, 2, or 3 positions by one or more suitable groups such as e.g. halogen (particularly F, Cl or Br); cyano; nitro; $C_{1-8}$ alkyl; $C_{1-8}$ alkoxy; $C_{1-8}$ alkylthio; $C_{1-8}$ alkylsulfonyl; $C_{2-8}$ alkenyl; $C_{2-8}$ alkynyl; hydroxyl; nitro; alkanoyl such as a $C_{1-6}$ alkanoyl e.g. acyl, haloalkyl particularly $C_{1-8}$ haloalkyl such as $CF_3$; —CONHR, —CONRR' where R and R' are optionally substituted $C_{1-8}$alkyl; —COOH, COC, >C═O; and the like.

Exemplary suitable monomers of Formula (I-1) are described below, but are not limited to these structures. For purposes of these structures, "$R_2$" and "X" are as defined above for Formula I-1.

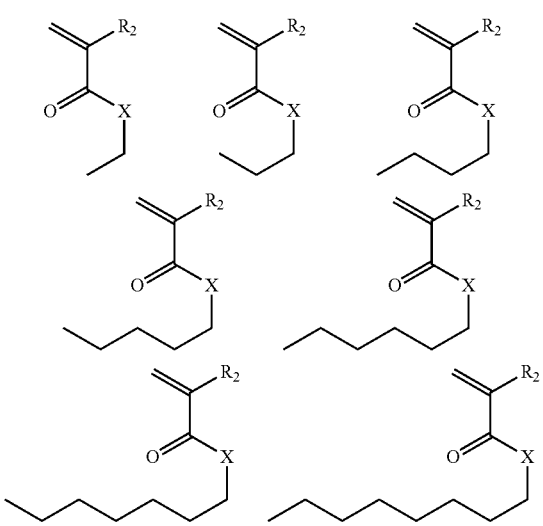

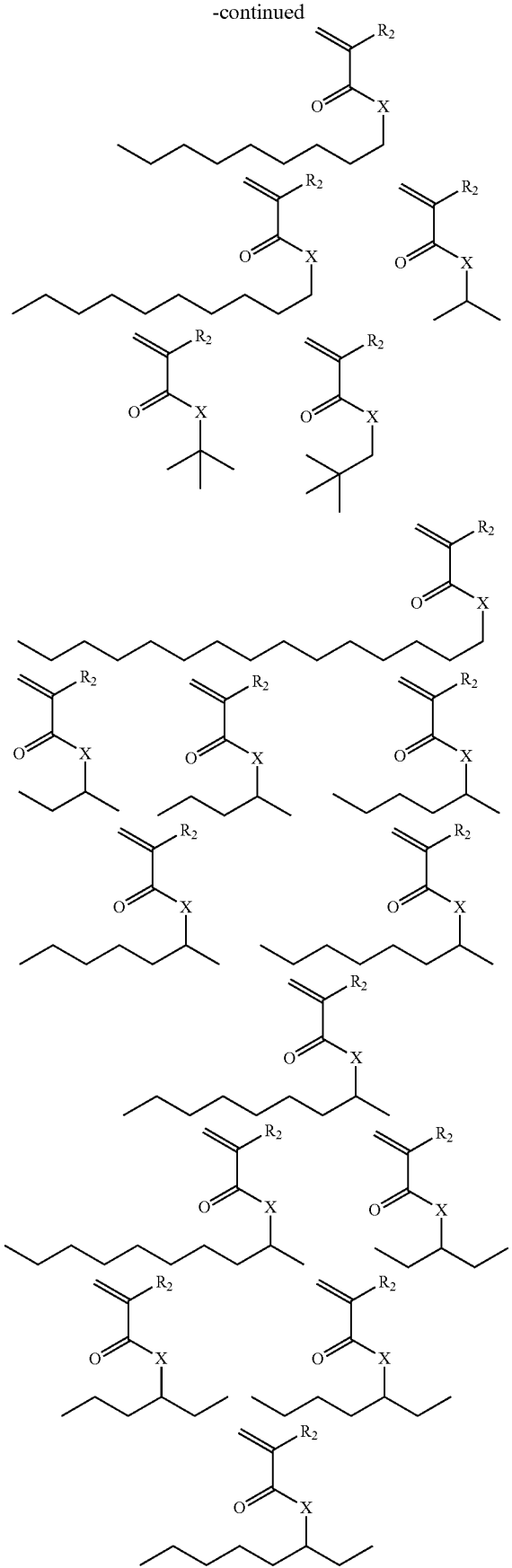
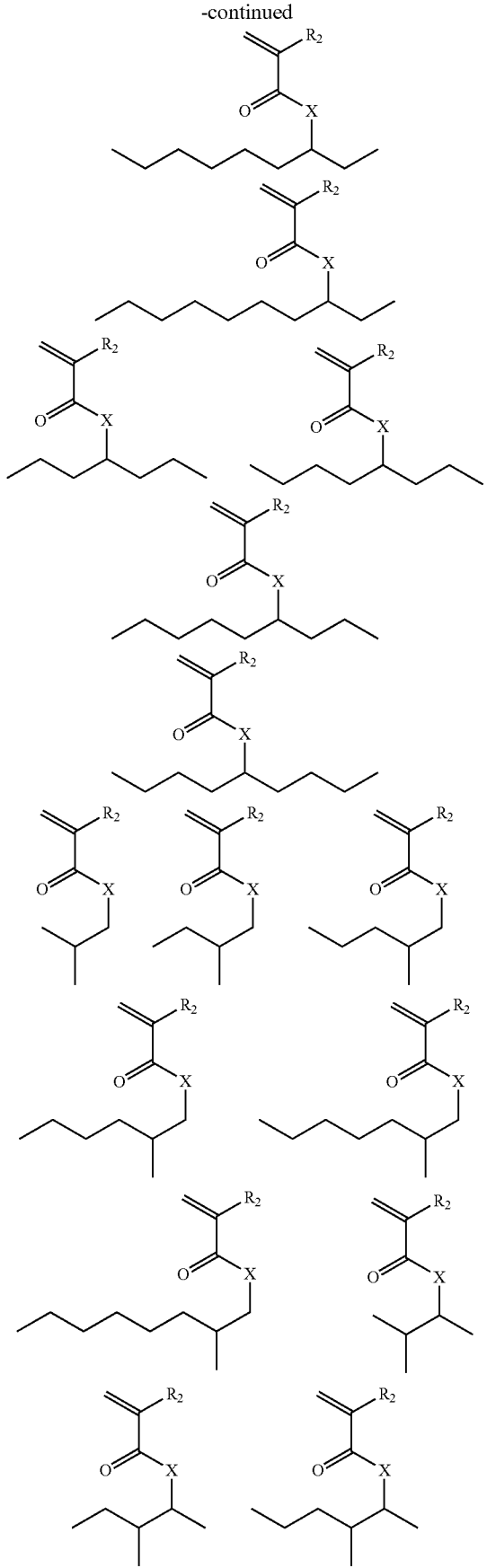

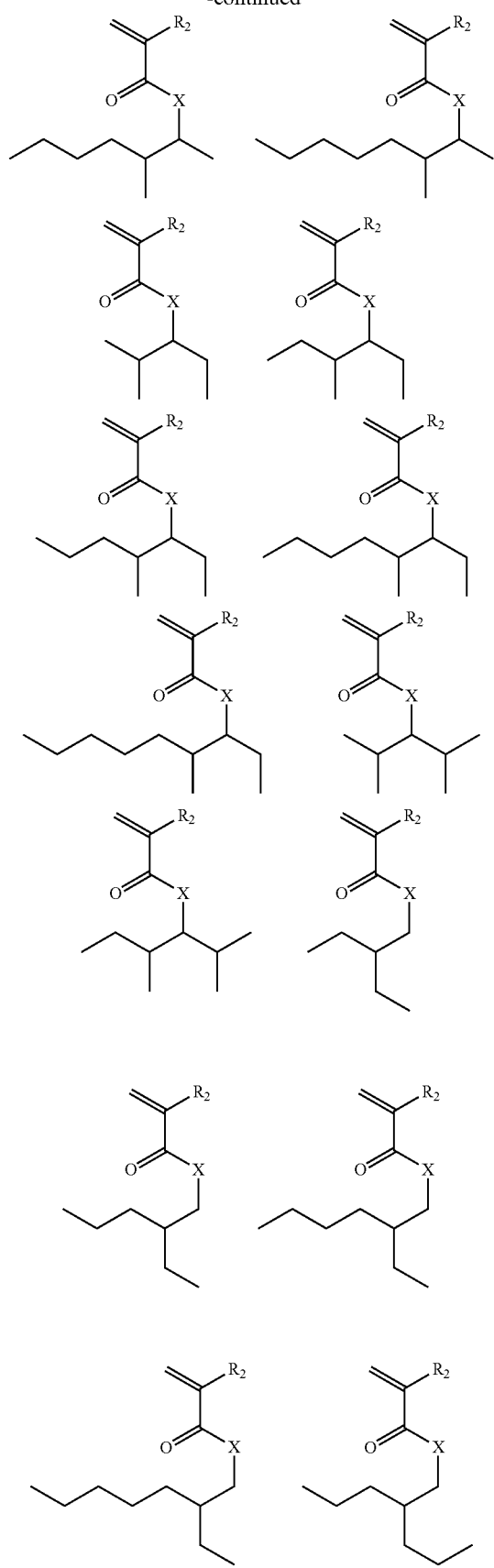
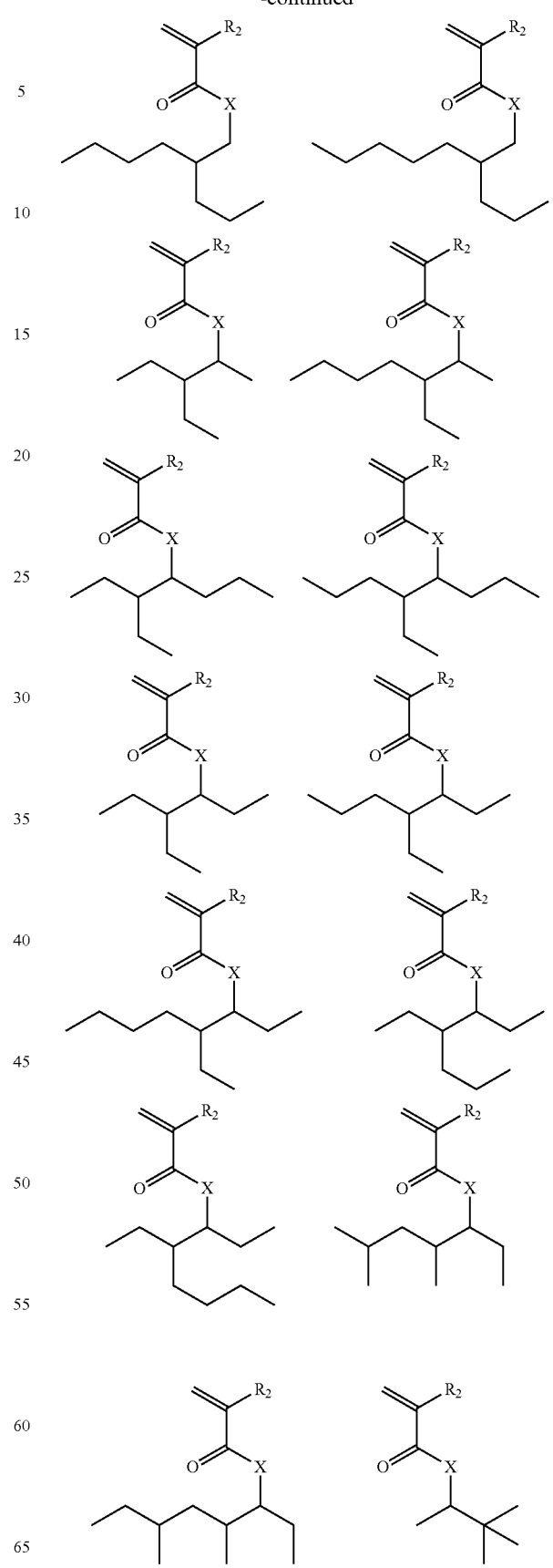

35
-continued
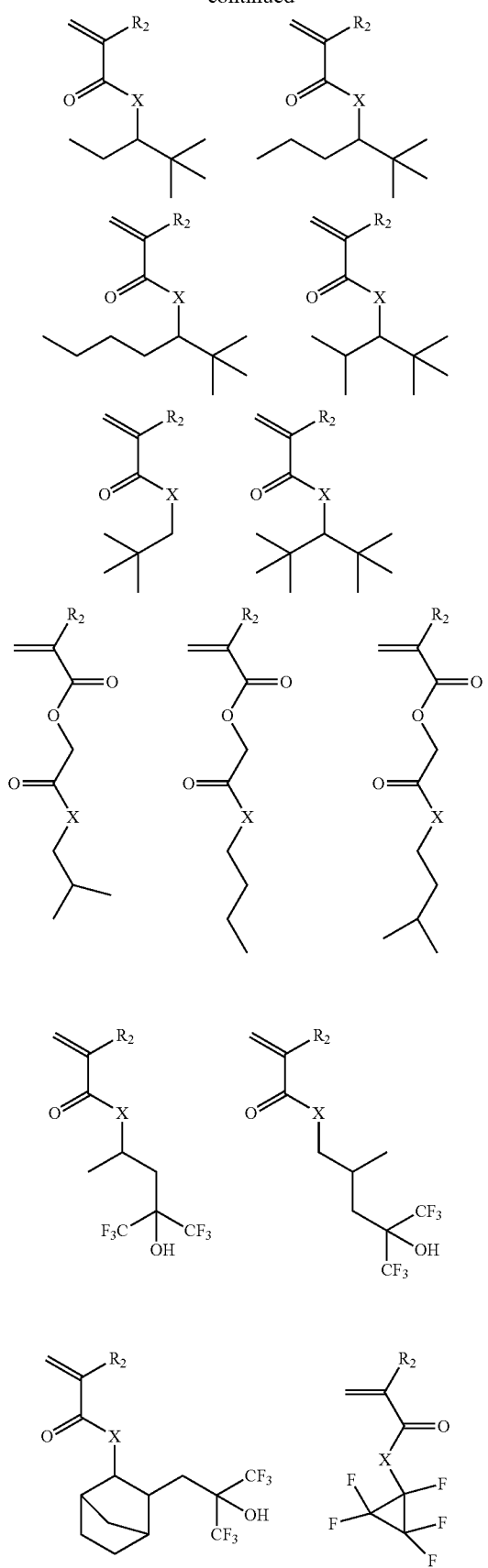
36
-continued
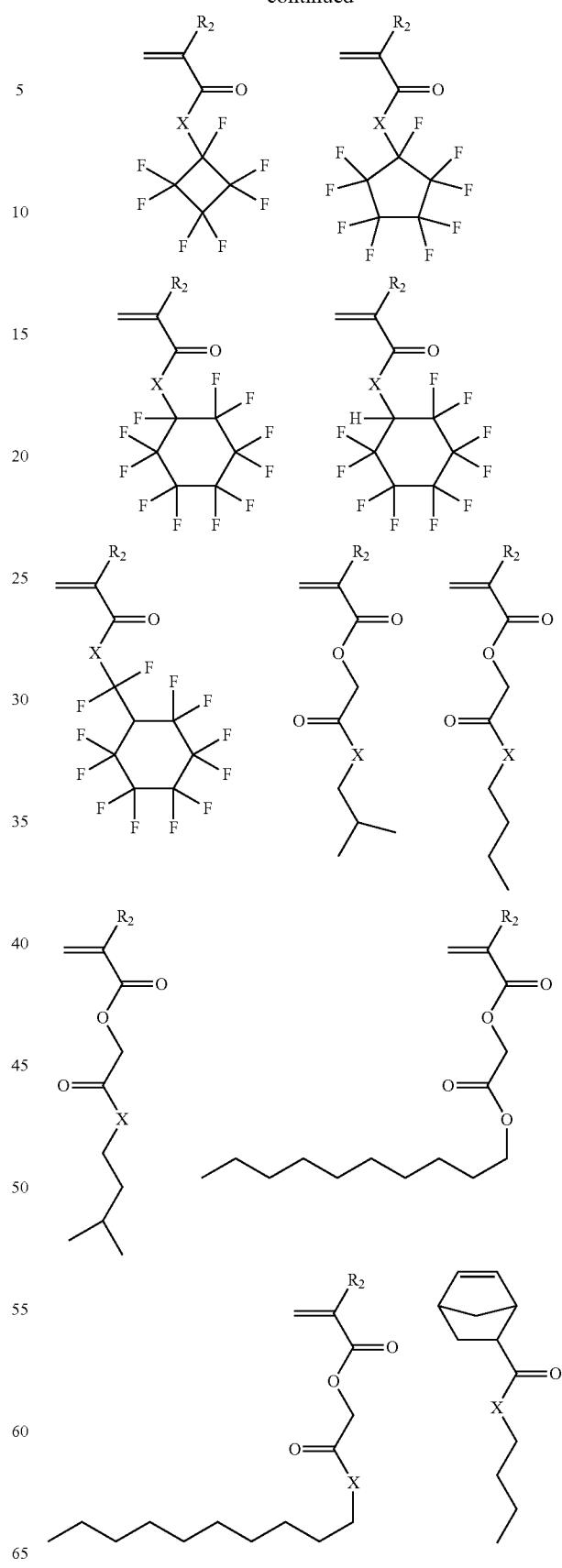

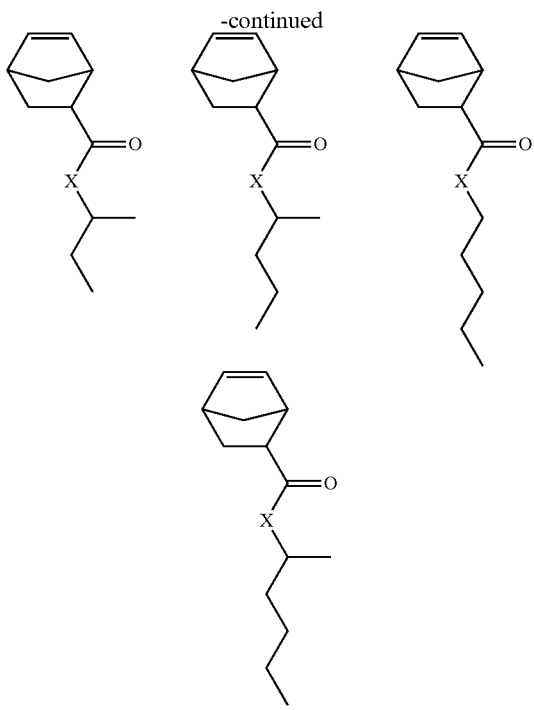

The photoresist compositions suitably include a single first polymer that comprises a structure of Formula (I), (IIA or (IIB), but can optionally include one or more additional first polymers.

The first polymer that comprises a structure of Formula (I), (IIA or (IIB) is typically present in the photoresist composition in a relatively small amount, for example, in an amount of from 0.1 to 10 wt %, preferably from 0.5 to 5 wt %, more preferably from 1 to 3 wt %, based on total solids of the photoresist composition. The content of the first or additive polymer will depend, for example, on the content of acid generator in the photoresist layer, the content of the nitrogen-containing groups in the first polymer, and whether the lithography is a dry or immersion-type process. For example, the first polymer lower limit for immersion lithography is generally dictated by the need to prevent leaching of the resist components. An excessively high first polymer content will typically result in pattern degradation. The weight average molecular weight of the additive polymer is typically less than 400,000, preferably from 3000 to 50,000, more preferably from 3000 to 25,000. Suitable first polymers and monomers for making the first polymers for use in the photoresist compositions of the invention are commercially available and/or can be made by persons skilled in the art.

The photosensitive composition preferably may comprise one or more photoacid generators (PAG) employed in an amount sufficient to generate a latent image in a coating layer of the photoresist composition upon exposure to activating radiation. For example, the photoacid generator will suitably be present in an amount of from about 1 to 20 wt % based on total solids of the photoresist composition. Typically, lesser amounts of the photoactive component will be suitable for chemically amplified resists.

Suitable PAGs are known in the art of chemically amplified photoresists and include, for example: onium salts, for example, triphenylsulfonium trifluoromethanesulfonate, (p-tert-butoxyphenyl)diphenylsulfonium trifluoromethanesulfonate, tris(p-tert-butoxyphenyl)sulfonium trifluoromethanesulfonate, triphenylsulfonium p-toluenesulfonate; nitrobenzyl derivatives, for example, 2-nitrobenzyl p-toluenesulfonate, 2,6-dinitrobenzyl p-toluenesulfonate, and 2,4-dinitrobenzyl p-toluenesulfonate; sulfonic acid esters, for example, 1,2,3-tris(methanesulfonyloxy)benzene, 1,2,3-tris(trifluoromethanesulfonyloxy)benzene, and 1,2,3-tris(p-toluenesulfonyloxy)benzene; diazomethane derivatives, for example, bis(benzenesulfonyl)diazomethane, bis(p-toluenesulfonyl)diazomethane; glyoxime derivatives, for example, bis-O-(p-toluenensulfonyl)-α-dimethylglyoxime, and bis-O-(n-butanesulfonyl)-α-dimethylglyoxime; sulfonic acid ester derivatives of an N-hydroxyimide compound, for example, N-hydroxysuccinimide methanesulfonic acid ester, N-hydroxysuccinimide trifluoromethanesulfonic acid ester; and halogen-containing triazine compounds, for example, 2-(4-methoxyphenyl)-4,6-bis(trichloromethyl)-1,3,5-triazine, and 2-(4-methoxynaphthyl)-4,6-bis(trichloromethyl)-1,3,5-triazine. One or more of such PAGs can be used.

Suitable solvents for the photoresist compositions of the invention include, for example: glycol ethers such as 2-methoxyethyl ether (diglyme), ethylene glycol monomethyl ether, and propylene glycol monomethyl ether; propylene glycol monomethyl ether acetate; lactates such as methyl lactate and ethyl lactate; propionates such as methyl propionate, ethyl propionate, ethyl ethoxy propionate and methyl-2-hydroxy isobutyrate; Cellosolve esters such as methyl Cellosolve acetate; aromatic hydrocarbons such as toluene and xylene; and ketones such as methylethyl ketone, cyclohexanone and 2-heptanone. A blend of solvents such as a blend of two, three or more of the solvents described above also are suitable. The solvent is typically present in the composition in an amount of from 90 to 99 wt %, more typically from 95 to 98 wt %, based on the total weight of the photoresist composition.

Other optional additives for the photoresist compositions include, for example, actinic and contrast dyes, anti-striation agents, plasticizers, speed enhancers, sensitizers, and the like. Such optional additives if used are typically present in the composition in minor amounts such as from 0.1 to 10 wt % based on total solids of the photoresist composition, although fillers and dyes can be present in relatively large concentrations, for example, from 5 to 30 wt % based on total solids of the photoresist composition.

A preferred optional additive of resist compositions of the invention is an added base which can enhance resolution of a developed resist relief image. Suitable basic quenchers include, for example: linear and cyclic amides and derivatives thereof such as N,N-bis(2-hydroxyethyl)pivalamide, N,N-Diethylacetamide, N1,N1,N3,N3-tetrabutylmalonamide, 1-methylazepan-2-one, 1-allylazepan-2-one and tert-butyl 1,3-dihydroxy-2-(hydroxymethyl)propan-2-ylcarbamate; aromatic amines such as pyridine, and di-tert-butyl pyridine; aliphatic amines such as triisopropanolamine, n-tert-butyldiethanolamine, tris(2-acetoxy-ethyl) amine, 2,2',2",2"'-(ethane-1,2-diylbis(azanetriyl))tetraethanol, and 2-(dibutylamino)ethanol, 2,2',2"-nitrilotriethanol; cyclic aliphatic amines such as 1-(tert-butoxycarbonyl)-4-hydroxypiperidine, tert-butyl 1-pyrrolidinecarboxylate, tert-butyl 2-ethyl-1H-imidazole-1-carboxylate, di-tert-butyl piperazine-1,4-dicarboxylate and N (2-acetoxy-ethyl) morpholine. Of these basic quenchers, 1-(tert-butoxycarbonyl)-4-hydroxypiperidine and triisopropanolamine are preferred. The added base is suitably used in relatively small amounts, for example, from 1 to 20 wt % relative to the PAG, more typically from 5 to 15 wt % relative to the PAG.

The photoresists used in accordance with the invention are generally prepared following known procedures. For example, a resist of the invention can be prepared as a coating composition by dissolving the components of the photoresist in a suitable solvent, for example, one or more of: a glycol ether such as 2-methoxyethyl ether (diglyme), ethylene glycol monomethyl ether, propylene glycol monomethyl ether; propylene glycol monomethyl ether acetate; lactates such as ethyl lactate or methyl lactate, with ethyl lactate being preferred; propionates, particularly methyl propionate, ethyl propionate and ethyl ethoxy propionate; a Cellosolve ester such as methyl Cellosolve acetate; an aromatic hydrocarbon such toluene or xylene; or a ketone such as methylethyl ketone, cyclohexanone and 2-heptanone. The desired total solids content of the photoresist will depend on factors such as the particular polymers in the composition, final layer thickness and exposure wavelength. Typically the solids content of the photoresist varies from 1 to 10 wt %, more typically from 2 to 5 wt %, based on the total weight of the photoresist composition.

The invention further provides methods for forming a photoresist relief image and producing an electronic device using photoresists of the invention. The invention also provides novel articles of manufacture comprising substrates coated with a photoresist composition of the invention.

In lithographic processing, a photoresist composition may be applied on a variety of substrates. The substrate can be of a material such as a semiconductor, such as silicon or a compound semiconductor (e.g., III-V or II-VI), glass, quartz, ceramic, copper and the like. Typically, the substrate is a semiconductor wafer, such as single crystal silicon or compound semiconductor wafer, and may have one or more layers and patterned features formed on a surface thereof. One or more layers to be patterned may be provided over the substrate. Optionally, the underlying base substrate material itself may be patterned, for example, when it is desired to form trenches in the substrate material. In the case of patterning the base substrate material itself, the pattern shall be considered to be formed in a layer of the substrate.

The layers may include, for example, one or more conductive layers such as layers of aluminum, copper, molybdenum, tantalum, titanium, tungsten, alloys, nitrides or silicides of such metals, doped amorphous silicon or doped polysilicon, one or more dielectric layers such as layers of silicon oxide, silicon nitride, silicon oxynitride, or metal oxides, semiconductor layers, such as single-crystal silicon, and combinations thereof. The layers to be etched can be formed by various techniques, for example, chemical vapor deposition (CVD) such as plasma-enhanced CVD, low-pressure CVD or epitaxial growth, physical vapor deposition (PVD) such as sputtering or evaporation, or electroplating. The particular thickness of the one or more layers to be etched 102 will vary depending on the materials and particular devices being formed.

Depending on the particular layers to be etched, film thicknesses and photolithographic materials and process to be used, it may be desired to dispose over the layers a hard mask layer and/or a bottom antireflective coating (BARC) over which a photoresist layer is to be coated. Use of a hard mask layer may be desired, for example, with very thin resist layers, where the layers to be etched require a significant etching depth, and/or where the particular etchant has poor resist selectivity. Where a hard mask layer is used, the resist patterns to be formed can be transferred to the hard mask layer which, in turn, can be used as a mask for etching the underlying layers. Suitable hard mask materials and formation methods are known in the art. Typical materials include, for example, tungsten, titanium, titanium nitride, titanium oxide, zirconium oxide, aluminum oxide, aluminum oxynitride, hafnium oxide, amorphous carbon, silicon oxynitride and silicon nitride. The hard mask layer can include a single layer or a plurality of layers of different materials. The hard mask layer can be formed, for example, by chemical or physical vapor deposition techniques.

A bottom antireflective coating may be desirable where the substrate and/or underlying layers would otherwise reflect a significant amount of incident radiation during photoresist exposure such that the quality of the formed pattern would be adversely affected. Such coatings can improve depth-of-focus, exposure latitude, linewidth uniformity and CD control. Antireflective coatings are typically used where the resist is exposed to deep ultraviolet light (300 nm or less), for example, KrF excimer laser light (248 nm) or ArF excimer laser light (193 nm). The antireflective coating can comprise a single layer or a plurality of different layers. Suitable antireflective materials and methods of formation are known in the art. Antireflective materials are commercially available, for example, those sold under the AR™ trademark by Rohm and Haas Electronic Materials LLC (Marlborough, Mass. USA), such as AR™40A and AR™124 antireflectant materials.

A photoresist layer formed from a composition of the invention as described above is applied on the substrate. The photoresist composition is typically applied to the substrate by spin-coating. During spin-coating, in resist compositions comprising both first and second polymers as disclosed herein, the first polymer in the photoresist segregates to the upper surface of the formed resist layer typically with intermixing with the second polymer in regions immediately below the upper surface. The solids content of the coating solution can be adjusted to provide a desired film thickness based upon the specific coating equipment utilized, the viscosity of the solution, the speed of the coating tool and the amount of time allowed for spinning A typical thickness for the photoresist layer is from about 500 to 3000 Å.

The photoresist layer can next be softbaked to minimize the solvent content in the layer, thereby forming a tack-free coating and improving adhesion of the layer to the substrate. The softbake can be conducted on a hotplate or in an oven, with a hotplate being typical. The softbake temperature and time will depend, for example, on the particular material of the photoresist and thickness. Typical softbakes are conducted at a temperature of from about 90 to 150° C., and a time of from about 30 to 90 seconds.

The photoresist layer is next suitably exposed to activating radiation through a photomask to create a difference in solubility between exposed and unexposed regions. References herein to exposing a photoresist composition to radiation that is activating for the composition indicates that the radiation is capable of forming a latent image in the photoresist composition. The photomask has optically transparent and optically opaque regions corresponding to regions of the resist layer to remain and be removed, respectively, in a subsequent development step. The exposure wavelength is typically sub-400 nm, sub-300 nm or sub-200 nm, with 248 nm, 193 nm and EUV wavelengths being typical. Photoresist materials can further be used with electron beam exposure. The methods find use in immersion or dry (non-immersion) lithography techniques. The exposure energy is typically from about 10 to 80 mJ/cm$^2$, dependent upon the exposure tool and the components of the photosensitive composition.

Following exposure of the photoresist layer, a post-exposure bake (PEB) is performed. The PEB can be conducted, for example, on a hotplate or in an oven. Conditions for the PEB will depend, for example, on the particular photoresist composition and layer thickness. The PEB is typically conducted at a temperature of from about 80 to 150° C., and a time of from about 30 to 90 seconds. A latent image defined by the boundary (dashed line) between polarity-switched and unswitched regions (corresponding to exposed and unexposed regions, respectively) is formed in the photoresist. The basic moiety (e.g. amine) of the first polymer deprotected during the post-expire bake is believed to prevent polarity switch in dark regions of the photoresist layer where stray or scattered light may be present, resulting in a latent image with vertical walls. This is a result of neutralization of acid generated by the PAG in the dark regions. As a result, cleavage of the acid-labile groups in those regions can be substantially prevented.

The exposed photoresist layer is next developed suitably to remove unexposed regions of the photoresist layer. An aqueous alkaline developer such as alkylammonium aqueous developer may be employed. Also, the developer may be an organic developer, for example, a solvent chosen from ketones, esters, ethers, hydrocarbons, and mixtures thereof. Suitable ketone solvents include, for example, acetone, 2-hexanone, 5-methyl-2-hexanone, 2-heptanone, 4-heptanone, 1-octanone, 2-octanone, 1-nonanone, 2-nonanone, diisobutyl ketone, cyclohexanone, methylcyclohexanone, phenylacetone, methyl ethyl ketone and methyl isobutyl ketone. Suitable ester solvents include, for example, methyl acetate, butyl acetate, ethyl acetate, isopropyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxypropionate, 3-methoxybutyl acetate, 3-methyl-3-methoxybutyl acetate, methyl formate, ethyl formate, butyl formate, propyl formate, ethyl lactate, butyl lactate and propyl lactate. Suitable ether solvents include, for example, dioxane, tetrahydrofuran and glycol ether solvents, for example, ethylene glycol monomethyl ether, propylene glycol monomethyl ether, ethylene glycol monoethyl ether, propylene glycol monoethyl ether, diethylene glycol monomethyl ether, triethylene glycol monoethyl ether and methoxymethyl butanol. Suitable amide solvents include, for example, N-methyl-2-pyrrolidone, N,N-dimethylacetamide and N,N-dimethylformamide. Suitable hydrocarbon solvents include, for example, aromatic hydrocarbon solvents such as toluene and xylene. In addition, mixtures of these solvents, or one or more of the listed solvents mixed with a solvent other than those described above or mixed with water can be used. Other suitable solvents include those used in the photoresist composition. The developer is preferably 2-heptanone or a butyl acetate such as n-butyl acetate.

The developer is typically applied to the substrate by spin-coating. The development time is for a period effective to remove the unexposed regions of the photoresist, with a time of from 5 to 30 seconds being typical. Development is typically conducted at room temperature. The development process can be conducted without use of a cleaning rinse following development. In this regard, it has been found that the development process can result in a residue-free wafer surface rendering such extra rinse step unnecessary.

The BARC layer, if present, is selectively etched using resist pattern as an etch mask, exposing the underlying hardmask layer. The hardmask layer is next selectively etched, again using the resist pattern as an etch mask, resulting in patterned BARC and hardmask layers. Suitable etching techniques and chemistries for etching the BARC layer and hardmask layer are known in the art and will depend, for example, on the particular materials of these layers. Dry-etching processes such as reactive ion etching are typical. The resist pattern and patterned BARC layer are next removed from the substrate using known techniques, for example, oxygen plasma ashing.

The following non-limiting examples are illustrative of the invention.

Examples 1-5

Synthesis of Monomer 1 to 5

Example 1

Synthesis of Monomer 1

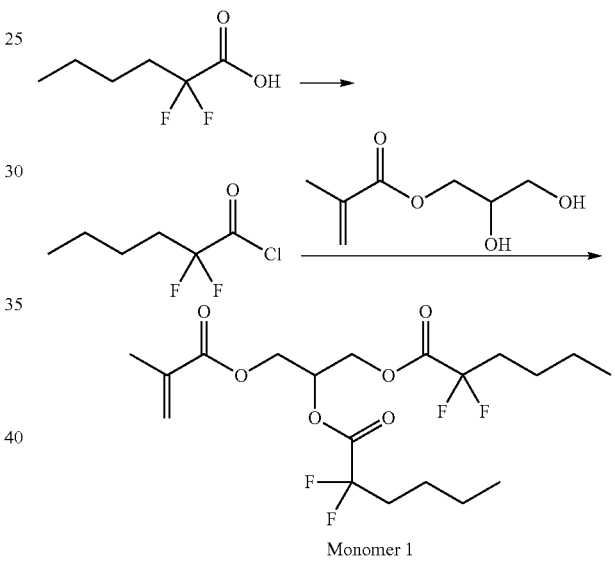

Monomer 1

2,2-Difluorohexanoic acid (50 g) was dissolved in 250 mL of methylene chloride into round-bottom flask at 0° C. under nitrogen atmosphere. Oxalyl chloride (27.6 mL) was added dropwise and 1 to drops of dimethyl formamide was added. The reaction mixture was slowly warmed to room temperature and allowed to stir at this temperature for 4 hours. No further work-up process was performed before the next step.

2,3-Dihydroxypropyl methacrylate (22.43 g) was dissolved in 100 mL and this solution was added to reaction mixture at 0° C. and thereafter pyridine (56.4 mL) was added slowly. The reaction mixture was slowly warmed to room temperature and allowed to stir at this temperature for 16 hours.

The reaction mixture was transferred to 200 mL of deionized water and the organic phase was washed with 1N HCl and aqueous sodium bicarbonate and deionized water consecutively, the collected organic solution was dried over sodium sulfate, filtered and concentrated in vacuo to provide Monomer 1 as depicted above.

Example 2

Synthesis of Monomer 2

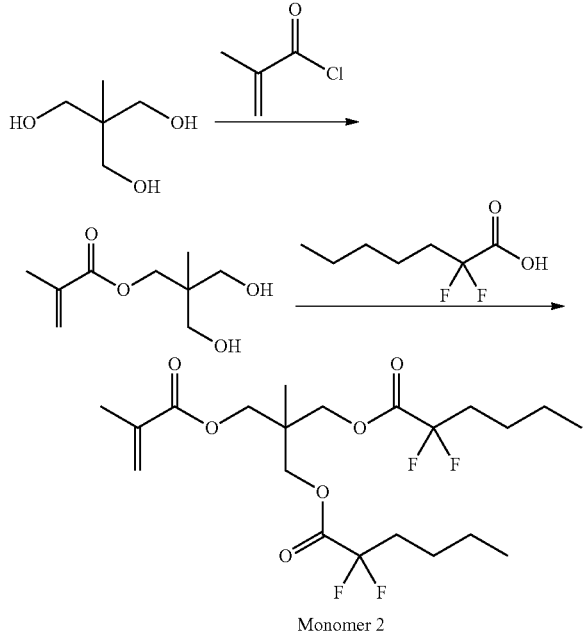

Monomer 2

1,1,1-Tris(hydroxymethyl)ethane (23 g, 191 mmol) and triethylamine (26.7 mL, 191 mmol) were dissolved in 100 mL of dimethylformamide into round-bottom flask under nitrogen atmosphere. Methacryloyl chloride (9.3 mL, 96 mol) was added dropwisely at 0° C. The reaction mixture was slowly warmed up to room temperature and allowed to stir at this temperature for 3 h. The reaction mixture was transferred to 100 mL of deionized water and extracted with ethyl acetate and the organic phase was washed with an aqueous NH$_4$Cl and deionized water consecutively. The collected organic solution was dried over sodium sulfate, filtered and concentrated in vacuo. Difluorohexanoic acid (14.23 g, 94 mmol) was added to round-bottom flask under nitrogen atmosphere. DCM (100 mL) was added as solvent, then DMF (0.2 mL) was injected. Oxalyl chloride (8 mL, 94 mmol) was added dropwisely. The solution was stirred at room temperature until the evolution of gas ceased. 2,2-bis (hydroxymethyl)propyl methacrylate (8.00 g, 43 mmol) was dissolved in DCM (40 mL) and pyridine (17.1 mL, 213 mmol), and the solution was transferred to dropping funnel. The solution was added dropwisely at 0° C. The reaction mixture was slowly warmed up to room temperature and allowed to stir at this temperature for 3 h. then. The reaction mixture was transferred to 100 mL of deionized water, then the organic layer was washed with 1N HCl and brine. The solution was dried over sodium sulfite, filtered and concentrated in vacuo to provide Monomer 2 as depicted above.

Example 3

Synthesis of Monomer 3

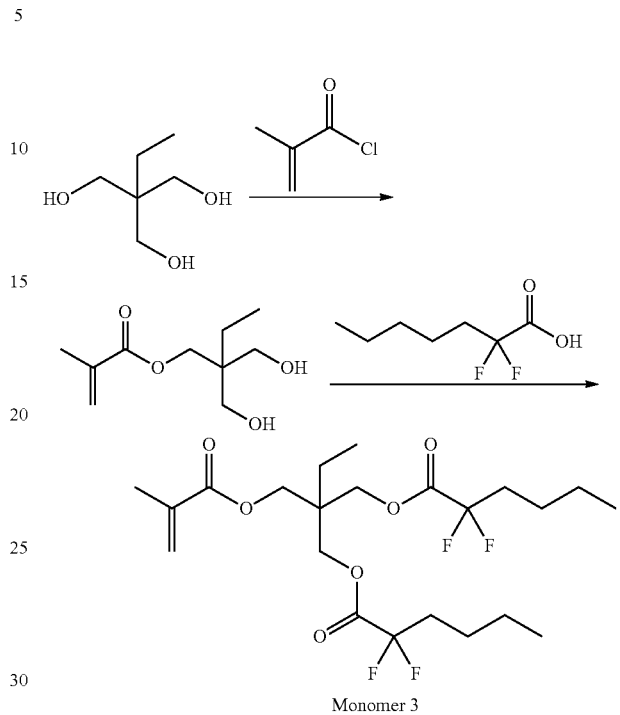

Monomer 3

1,1,1-Tris(hydroxymethyl)propane (25.67 g, 191 mmol) and triethylamine (26.7 mL, 191 mmol) were dissolved in 100 mL of dimethylformamide into round-bottom flask under nitrogen atmosphere. Methacryloyl chloride (9.3 mL, 96 mol) was added dropwise at 0° C. The reaction mixture was slowly warmed up to room temperature and allowed to stir at this temperature for 3 h. The reaction mixture was then transferred to 100 mL of deionized water and extracted with ethyl acetate and the organic phase was washed with an aqueous NH$_4$Cl and deionized water consecutively. The collected organic solution was dried over sodium sulfate, filtered and concentrated in vacuo. Difluorohexanoic acid (14.23 g, 94 mmol) was added to round-bottom flask under nitrogen atmosphere. DCM (100 mL) was added as solvent, then DMF (0.2 mL) was injected. Oxalyl chloride (8 mL, 94 mmol) was added dropwisely. The solution was stirred at room temperature until the evolution of gas ceased. 2,2-bis (hydroxymethyl)butyl methacrylate (8.6 g, 43 mmol) was dissolved in dichloromethane (40 mL) and pyridine (17.1 mL, 213 mmol), and the solution was transferred to dropping funnel. The solution was added dropwisely at 0° C. The reaction mixture was slowly warmed up to room temperature and allowed to stir at this temperature for 3 h. then. The reaction mixture was transferred to 100 mL of deionized water, then the organic layer was washed with 1N HCl and brine. The solution was dried over sodium sulfate, filtered and concentrated in vacuo to provide Monomer 3 as depicted above.

Example 4

Synthesis of Monomer 4

Part A: Synthesis of Monomer Precursor

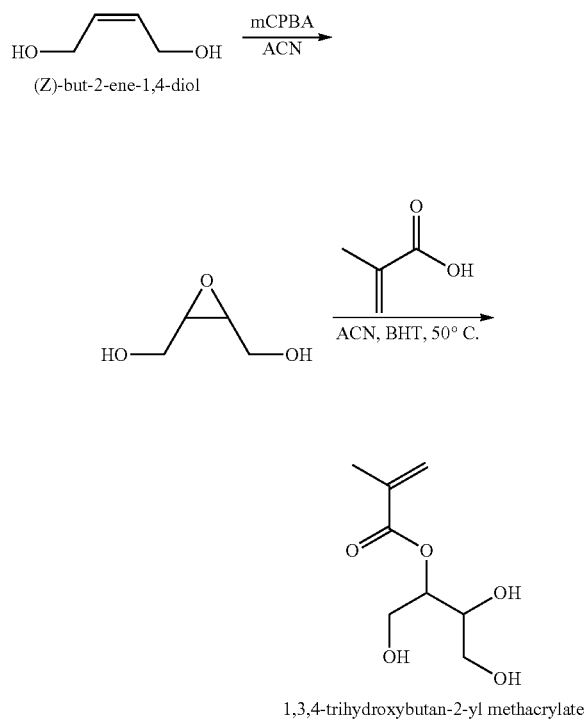

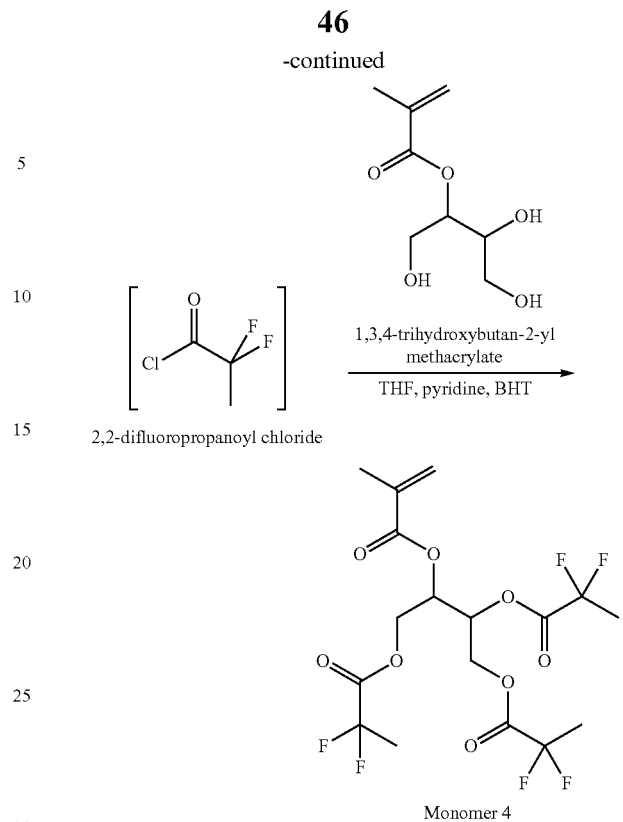

Preparation of a cold solution of (Z)-but-2-ene-1,4-diol (50 g, 567.47 mmol) in CH3CN (650 mL) was added m-chloroperbenzoic acid (144 g, 584.49 mmol). The mixture was stirred at from 0° C. to rt for 24 h. The benzoic acid formed was removed by filtration and the filtrate was washed with diethyl ether to remove the unreacted m-chloroperbenzoic acid and the remaining chlorobenzoic acid. The product was isolated from the solution by diethyl ether to provide 51.5 g (85%). Oxirane 2,3 diyldimethanol (5 g, 48.02 mmol), methacrylic acid (8.68 g, 100.84 mmol, triethyl amine (0.7 ml, 0.4.80 mmol), BHT (catalyst amounts) were added to CH$_3$CN in a RBF fitted with a condenser. The reaction mixture was stirred for 48 h at 50° C. After the reaction mixture evaporated under reduced pressure and washed with diethyl ether to remove the residual methacrylic acid. The product 1,3,4-trihydroxybutan-2-yl methacrylate was obtained.

Part B: Synthesis of Monomer 4

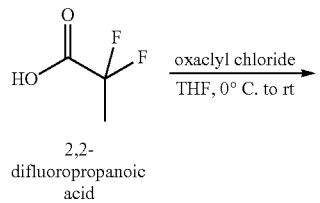

Oxaclyl chloride (0.5 ml, 5.80 mmol) and catalytic amounts of DMF was added to a solution of 2,2-difluoropropanoic acid (0.58 g, 5.27 mmol) in dry THF (6 mL) was added. The mixture was stirred at 0° C. for 2 h. After a solution of 1,3,4-trihydroxybutan-2-yl methacrylate (0.25 g, 1.39 mmol), pyridine(0.53 ml, 6.59 mmol) in dry THF (5 ml) was added a solution of 2,2-difluoropropanoyl chloride in THF. The mixture was stirred to warm for 16 h. After the reaction mixture was cooled to 0° C. and quenching with water. The layers were separated and aqueous layer was extracted with ethyl acetate. The organic layer was combined washed with 1N HCl solution and brine, filtered through Na$_2$SO$_4$ and evaporated under reduced pressure. The crude product was purified to obtain the ester compound Monomer 4 as depicted above.

Example 5

Synthesis of Monomer 5

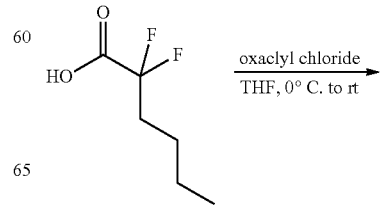

-continued

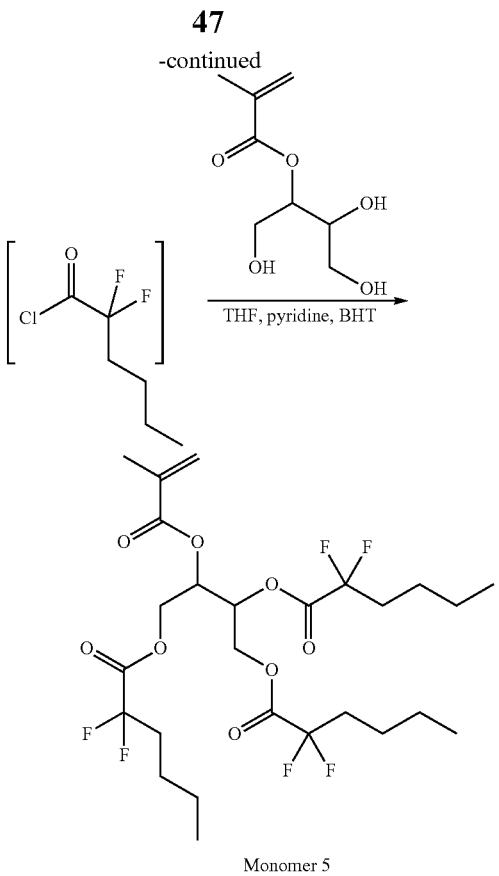

Monomer 5

Oxaclyl chloride (21.8 ml, 254.5 mmol) and catalytic amounts of DMF was added to a solution of 2,2-difluorohexanoic acid (35.26 g, 231.3 mmol) in dry MC (100 mL) was added. The mixture was stirred at 0° C. for 2 h. After a solution of 1,3,4-trihydroxybutan-2-yl methacrylate (11 g, 27.8 mmol), pyridine(23.3 ml, 289.2 mmol) in dry MC (40 ml) was added a solution of 2,2-difluorohexanoyl chloride in MC. The mixture was stirred to warm for 16 h. After the reaction mixture was cooled to 0° C. and quenching with water. The layers were separated and aqueous layer was extracted with MC. The organic layer was combined washed with 1N HCl solution and brine, filtered through $Na_2SO_4$ and evaporated under reduced pressure. The crude product was purified to obtain the ester compound Monomer 5 as depicted above.

Example 6

Synthesis of Monomer 6

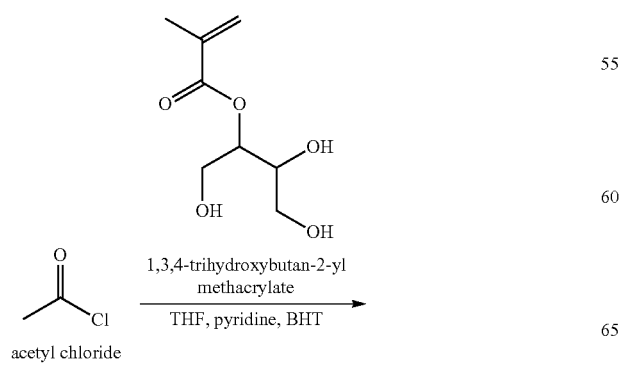

-continued

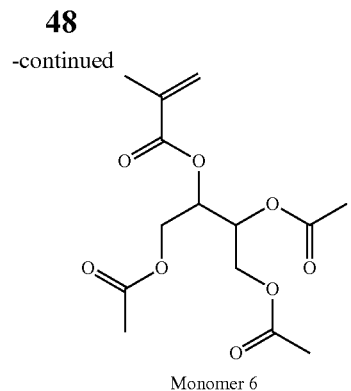

Monomer 6

Preparation of a solution of 1,3,4-trihydroxybutan-2-yl methacrylate (0.21 g, 1.10 mmol), pyridine (0.53 ml, 6.65 mmol) in dry THF (5 ml) was added a acetyl chloride (0.4 ml, 5.54) at 0° C. The mixture was stirred to warm for 16 h. After the reaction mixture was cooled to 0° C. and quenching with water. The layers were separated and aqueous layer was extracted with ethyl acetate. The organic layer were combined washed with 1N HCl solution and brine, filtered through $Na_2SO_4$ and evaporated under reduced pressure. The crude product was purified to obtain the ester compound Monomer 6 as depicted above.

Examples 7-12

Syntheses of Polymer 1 to 7

Example 7

Synthesis of Polymer 2

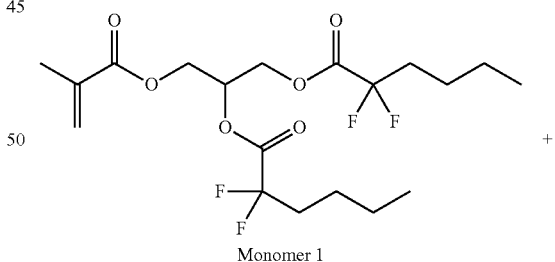

Monomer 1

+

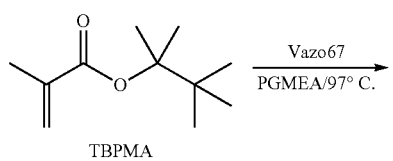

TBPMA

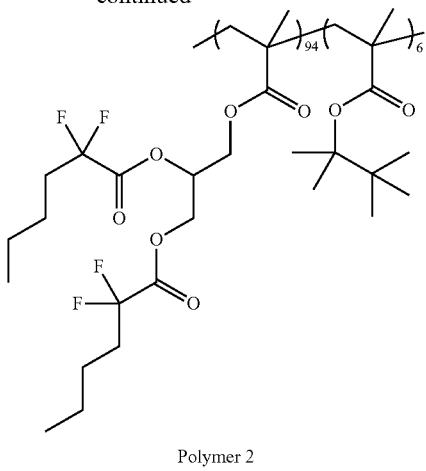

Polymer 2

13.16 g of synthesized monomer, 0.84 g of TBPMA monomer and 7.0 g PGMEA were added to a glass bottle. Slightly shake the bottle to mix its content and then place the bottle in an ice bath to reach temperature equilibrium with the ice bath. 0.29 g of initiator (vazo67, white powder) was added reaction bottle and place into the ice bath. 7.0 g of PGMEA was charge to 100 ml of three-neck round bottom with condenser. A thermo-couple was reached to the reaction mixtures for measuring and controlling the reaction temperature of the solvent throughout the polymerization. After the feeding solution was delivered through feeding inlet, the reactor was heated to 97° C.±2° C. Once the reaction temperature of reaction mixtures was reached to the setting temperature (97° C.), the feeding solution was fed into the reactor with 250 µl over 13 sec of feeding rate during up to 75 min of total feeding time. After feeding, the reactor was maintained at 97° C. for additional 2 hours and the reaction mixture was cooled to room temperature with stirring. The average molecular weight and polydispersity of Polymer 2 (depicted above) was 14.7 K and 1.80 respectively.

Example 8

Synthesis of Polymer 3

The procedures of Example 7 were repeated for synthesizing Polymer 3 with Monomer 1 except the amount of initiator was 0.31 g. The average molecular weight and polydispersity of Polymer 3 was 8.2K and 1.63 respectively. Thus, Polymer 3 has the same structure as Polymer 2 shown in Example 7 above except for the differences of molecular weight and polydispersity.

Example 9

Synthesis of Polymer 4

The procedures of Example 7 were repeated for synthesizing Polymer 4 with Monomer 1 except the amount of initiator was 0.32 g. The average molecular weight and polydispersity of Polymer 4 was 5.4K and 1.46 selectively. Thus, Polymer 4 has the same structure as Polymer 2 shown in Example 7 above except for the differences of molecular weight and polydispersity.

Example 10

Synthesis of Polymer 5

The procedures of Example 7 were repeated for synthesizing Polymer 5 except Monomer 2 of Example 2 was substituted for Monomer 1. The average molecular weight and polydispersity of Polymer 5 was 10.6K and 1.76 respectively.

Example 10

Synthesis of Polymer 6

The procedures of Example 7 were repeated for synthesizing Polymer 6 except Monomer 3 of Example 3 was substituted for Monomer 1. The average molecular weight and polydispersity of Polymer 6 was 10.0K and 1.61 respectively.

Example 11

Synthesis of Polymer 7

The procedures of Example 7 were repeated for synthesizing Polymer 7 except Monomer 5 of Example 5 was substituted for Monomer 1. The average molecular weight and polydispersity of Polymer 7 was 7.0K and 1.44 selectively.

Example 12

Synthesis of Reference Polymer 1

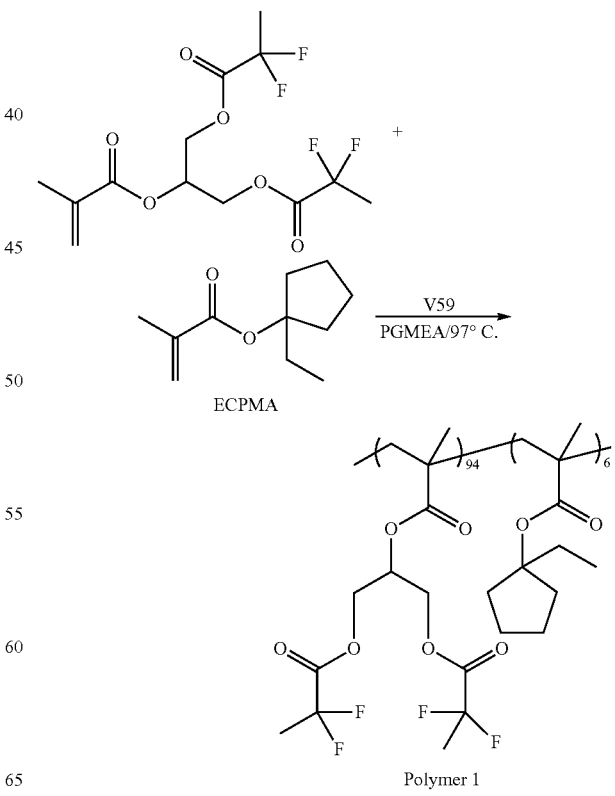

Polymer 1

By general procedures of Example 7 above, Polymer 1 as shown in the above scheme was prepared.

Example 13

Water Contact Angle Analysis

Water contact angles (WCA) were evaluated for the spin-coated layers of the polymers as specified in Table 1 below. In Table 1, Polymers 1 through 7 correspond to the same-named polymers of Examples 7-12 above. Several water contact angles were evaluated: static, receding, advancing, sliding, and tilt in general accordance with the procedures disclosed in Burnett et al., *J. Vac. Sci. Techn. B*, 23(6), pages 2721-2727 (November/December 2005). The results set forth in Table 1 below show that both polymers and photoresist compositions of the invention can be prepared to achieve desired water angles, as may be desired by device manufacturers, such as a receding water contact angle of in excess of 64, 65, 66, 67, 68, 69, 70, 71, 72, 0 or 75 and/or a sliding water contact angle of less than 20 degrees for both polymers and photoresist compositions.

TABLE 1

|  | 3% Polymer 1 | 3% Polymer 2 | 3% Polymer 3 | 3% Polymer 4 | 3% Polymer 5 | 3% Polymer 6 | 3% Polymer 7 |
| --- | --- | --- | --- | --- | --- | --- | --- |
| Static WCA | 81.0 | 96.4 | 92.6 | 90.8 | 94.4 | 93.7 | 93.9 |
| Advancing WCA | 86.6 | 97.1 | 100.9 | 93.1 | 95.5 | 96.2 | 99.8 |
| Receding WCA | 70.4 | 76.8 | 76.3 | 69.5 | 80.4 | 97.3 | 78.5 |
| Tilt WCA | 16.6 | 21.5 | 24.6 | 24.9 | 16.6 | 17.9 | 23.0 |

Examples 14-15

Preparation of Photoresist Compositions

Example 14

Preparation of Photoresist A

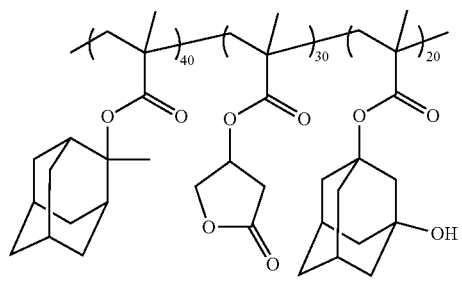

methyladamantylmethylacrylate/α-gammabutyrolactone/hydroxyadmantylmethylacrylate (40/30/20 respective weight ratio of the respective repeat units: methyladamantylmethylacrylate/α-gammabutyrolactone/hydroxyadmantylmethylacrylate)

A photoresist composition (designated herein as Photoresist A) was prepared by admixing 2.338 g of methyladamantylmethylacrylate/α-gammabutyrolactone/hydroxyadmantylmethylacrylate (approximately 9,0000 weight average molecular weight, polymer structure depicted above), 0.343 g of the photoacid generator triphenylsulfonium perfluorobutylsulfonate, 0.035 g of trioctyl amine, 0.353 g of Polymer 1 (23.8 wt % in PGMEA), 48.331 g of PGMEA and 48.600 g of methyl-2-hydroxyiosbutyrate (HBM) in a 250 ml polypropylene (PP) bottle. The PP bottle was shaken in room temperature for 6 hours.

Example 15

Preparation of Photoresist B

A photoresist composition (designated herein as Photoresist B) was prepared by admixing 2.338 g of of methyladamantylmethylacrylate/α-gammabutyrolactone/hydroxyadmantylmethylacrylate (approximately 9,0000 weight average molecular weight, polymer structure depicted above in Example 14), 0.343 g of TPS-PFBuS, 0.0.035 g of triocylamine, 0.175 g of Polymer 2 (48.1 wt % in PGMEA), 48.509 g of PGMEA and 48.600 g of HBM in a 250 ml PP bottle. The PP bottle was shaken in room temperature for 6 hours.

Example 16

Lithography—Photoresist A 300 mm HMDS-primed silicon wafers are spin-coated with AR™26N (Rohm and Haas Electronic Materials) to form a first bottom anti-reflective coating (BARC) on a TEL CLEAN TRAC LITHIUS i+, followed by the bake process for 60 seconds at 205° C.

A photoresist composition of Example 14 (Photoresist B) is spin-coated over the BARC layer. The thus applied photoresist layer is then soft-baked and imaged in an immersion lithography system with patterned radiation having a wavelength of 193 nm and image focus of −012. Other imaging parameters are set forth in Table 2 below. The exposed wafers are post-exposure baked at 90° C. for 60 seconds and then developed using tetraTMAH developer for approximately 30 seconds to give a photoresist relief image of well-resolved lines/spaces. Results are shown in the Table 2 following Example 17 below.

Example 17

Lithography—Photoresist B 300 mm HMDS-primed silicon wafers are spin-coated with AR™26N (Rohm and Haas Electronic Materials) to form a first bottom anti-reflective coating (BARC) on a TEL CLEAN TRAC LITHIUS i+, followed by the bake process for 60 seconds at 205° C.

A photoresist composition of Example 15 (Photoresist B) is spin-coated over the BARC layer. The thus applied photoresist layer is then soft-baked and imaged in an immersion lithography system with patterned radiation having a wavelength of 193 nm and image focus of −012. Other imaging parameters are set forth in Table 2 below. The exposed wafers are post-exposure baked at 90° C. for 60 seconds and then developed using TMAH developer for approximately 30 seconds to give a photoresist relief image of well-resolved lines/spaces. Results are as are set forth in the Table 2 below.

TABLE 2

| | Example 16 imaging results | Example 17 imaging results |
|---|---|---|
| Target CD (nm) @ 43 nm line/92 nm pitch | 43.6 | 43.3 |
| Esize (mJ) | 21.0 | 20.9 |
| EL %@ ±5% of Target CD | 23.1 | 22.7 |
| EL[nm/mJ]@ ±5% of Target CD | 0.9 | 0.9 |
| FL (nm) | 180~210 | 180~210 |
| LWR (3σ) | 1.87 | 1.67 |

In Table 2, Exposure latitude (EL), which defined as a difference in exposure energy to print +/−5% of the target CD (critical dimension) normalized by the sizing energy. Line width roughness (LWR) is the deviation in the width of a line measured over a given length. LWR is quantified as the 3σ deviation of the width. FL designates focus latitude. Esize was determined by the exposure doses required to provide a 1:1 resolution at the top and bottom of a 43 nm line-and-space pattern.

What is claimed is:

1. A polymer comprising a structure of the following Formula (I):

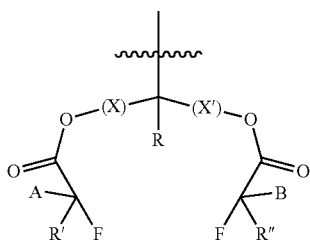

wherein:
X and X' are the same or different linker;
R is a non-hydrogen substituent; and
A and B are each independently hydrogen or fluorine;
R' and R" are each independently hydrogen or a non-hydrogen substituent,
with at least one of R' and R" being a non-hydrogen substituent other than a halogen or a halogen-substituted group.

2. A polymer of claim 1 wherein R' and R" are each independently hydrogen, fluorine, halogenated alkyl, non-halogenated alkyl, or heteroalkyl.

3. A polymer of claim 1 wherein X and X' are different.

4. A polymer of claim 1 wherein X and X' are the same.

5. A polymer of claim 1 wherein at least one of X and X' is —CH$_2$—.

6. A polymer of claim 1 comprising a structure of the following Formula (IIB)

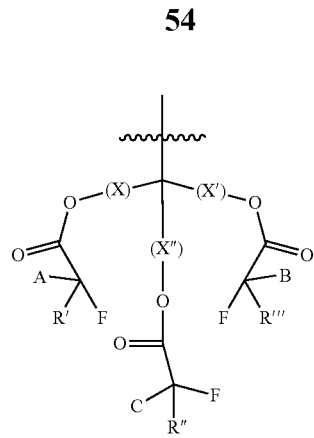

wherein in Formula (IIB):
X, X' and X" are each the same or different linker;
A, B and C are each independently hydrogen or fluorine; and
R', R" and R'" are each independently hydrogen or a non-hydrogen substituent.

7. A polymer of claim 1 wherein the polymer comprises acrylate units.

8. A polymer of claim 1 wherein the polymer comprises units obtained by polymerization of one or more monomers of the following Formula (III):

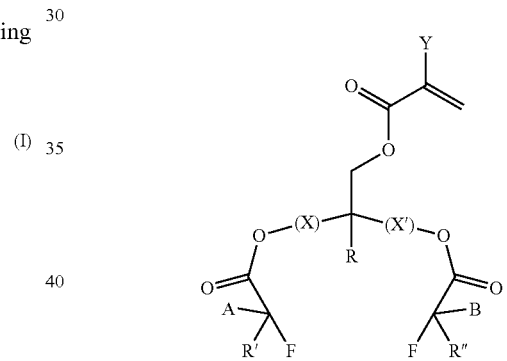

wherein in Formula (III):
Y is optionally substituted alkyl;
X and X' are the same or different linker;
R is a non-hydrogen substituent;
A and B are each independently hydrogen or fluorine; and
R' and R" are each independently hydrogen or a non-hydrogen substituent,
with at least one of R' and R" being a non-hydrogen substituent other than a halogen or a halogen-substituted group.

9. A polymer of claim 1 wherein at least one of A and B is fluorine.

10. A photoresist composition comprising a photoactive component and a polymer of claim 1.

11. A photoresist composition of claim 10 further comprising a second distinct polymer.

12. A method of processing a photoresist composition, comprising:
applying a layer of a photoresist composition of claim 10 on a substrate;
exposing the photoresist composition layer to activating radiation; and developing the exposed photoresist composition to provide a photoresist relief image.
13. The method of claim 12 wherein the photoresist composition layer is immersion exposed.
14. A photoresist composition comprising
a photoactive component and a polymer of claim 6.
15. A polymer comprising a polymerized monomer of one of the following structures:
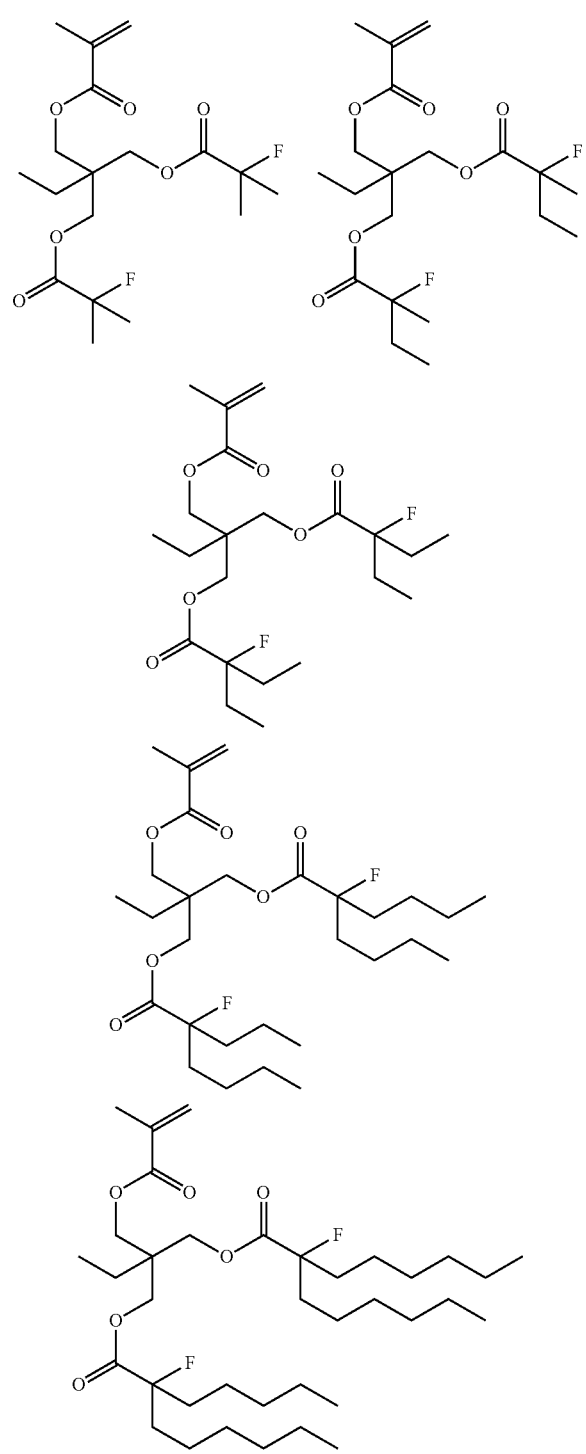
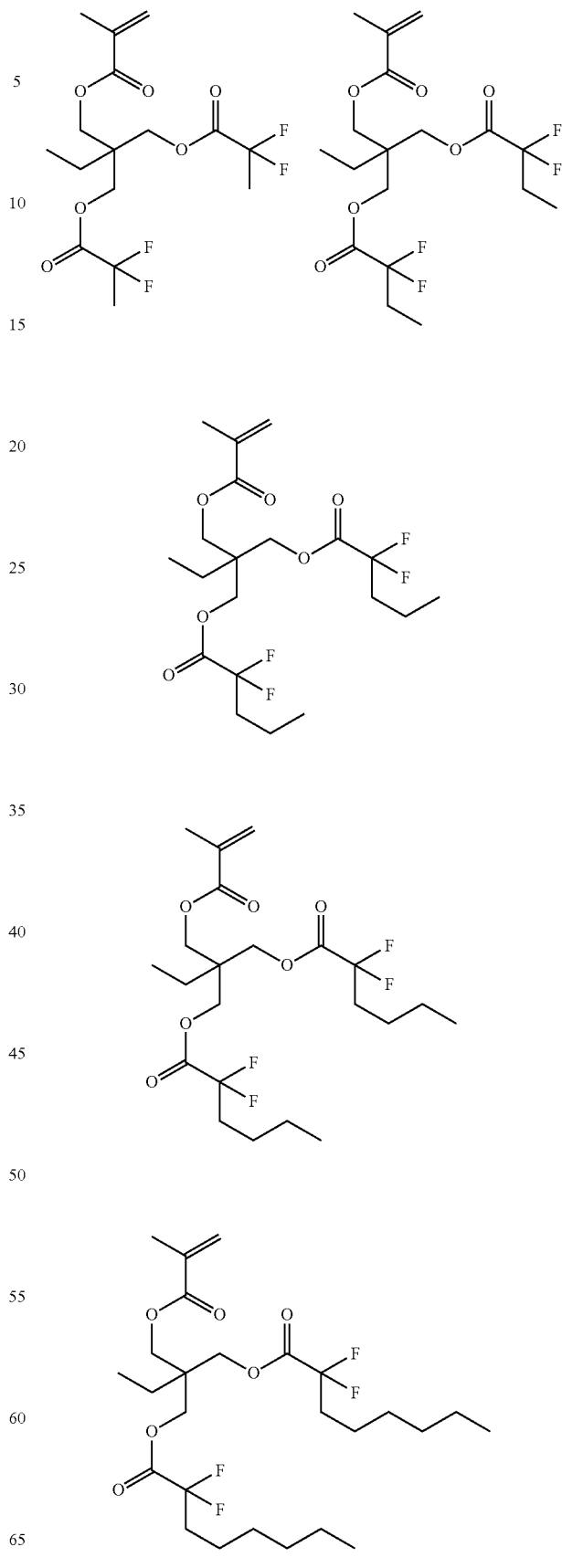

57
-continued
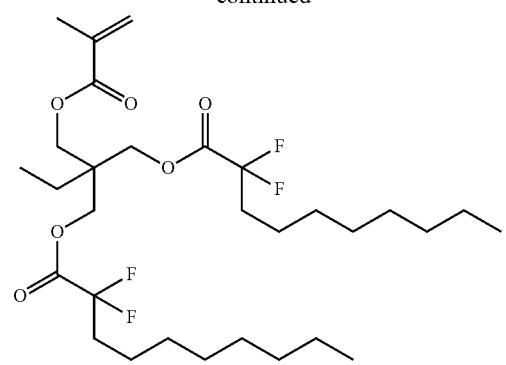
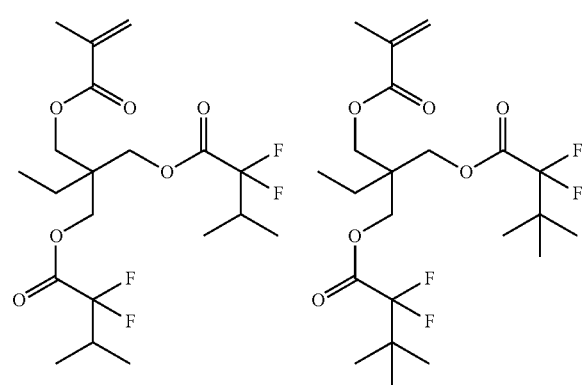
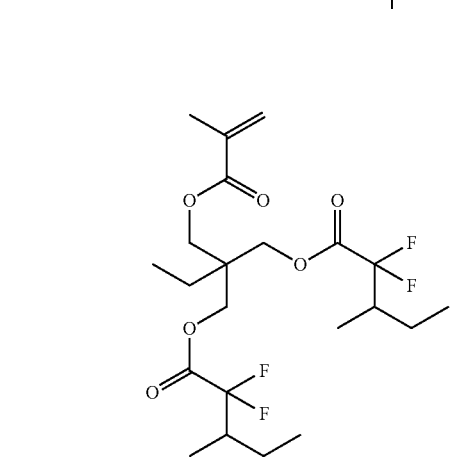
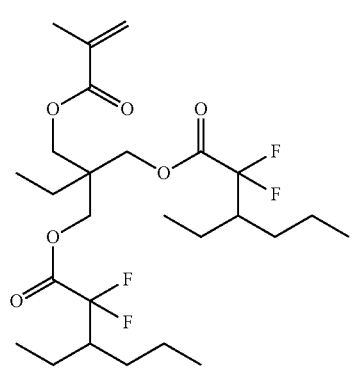
58
-continued
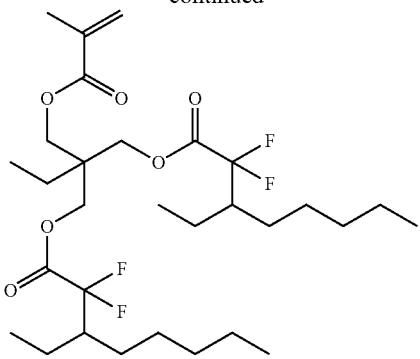
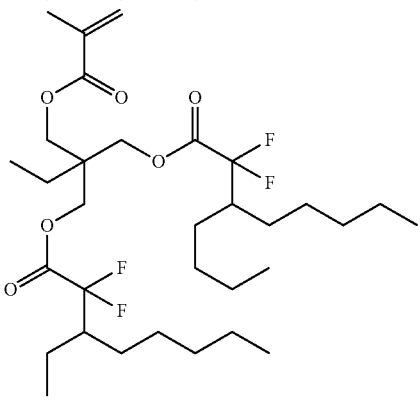
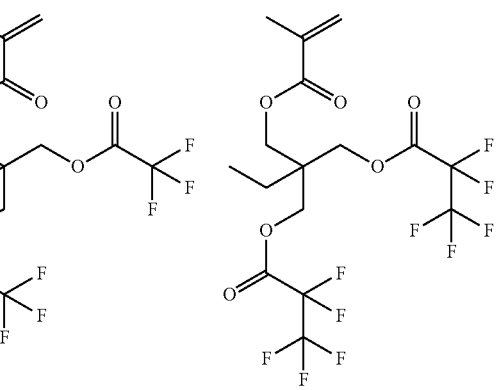
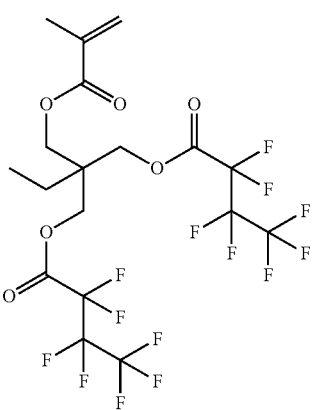

59
-continued
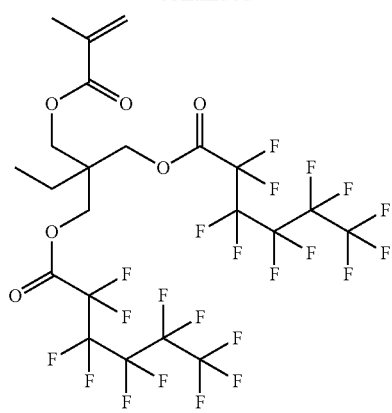
60
-continued
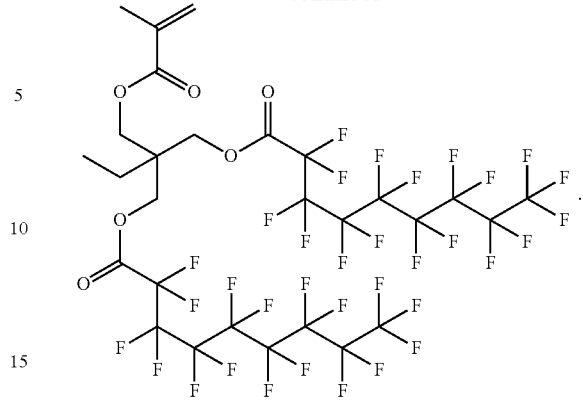
16. A polymer of claim 6 wherein the polymer comprising a polymerized monomer of one of the following structures:
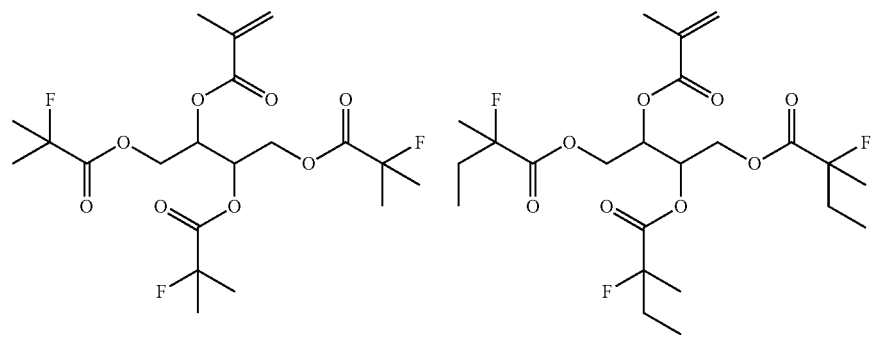
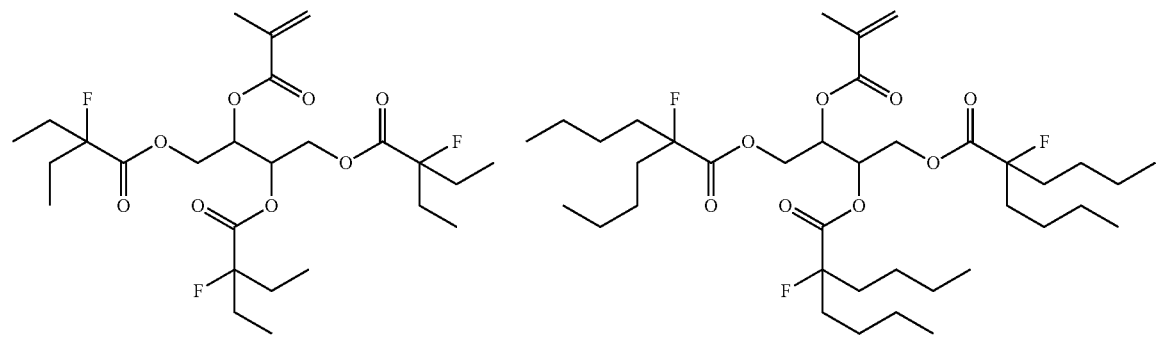
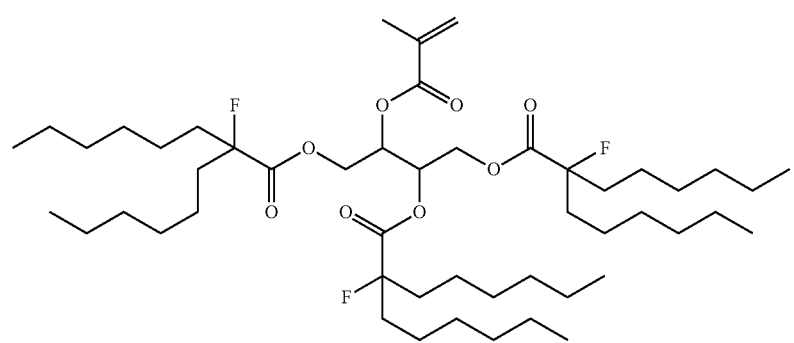

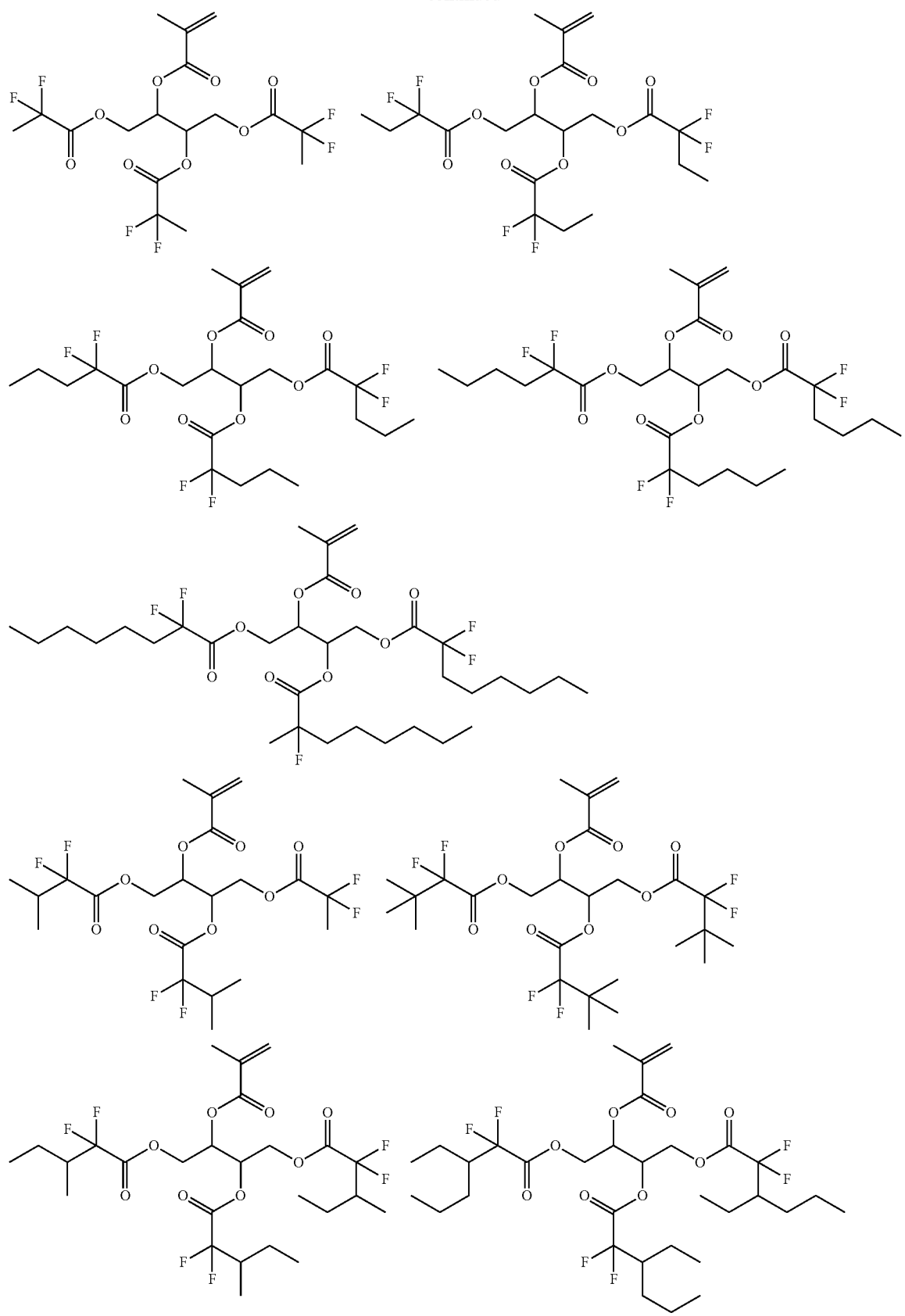

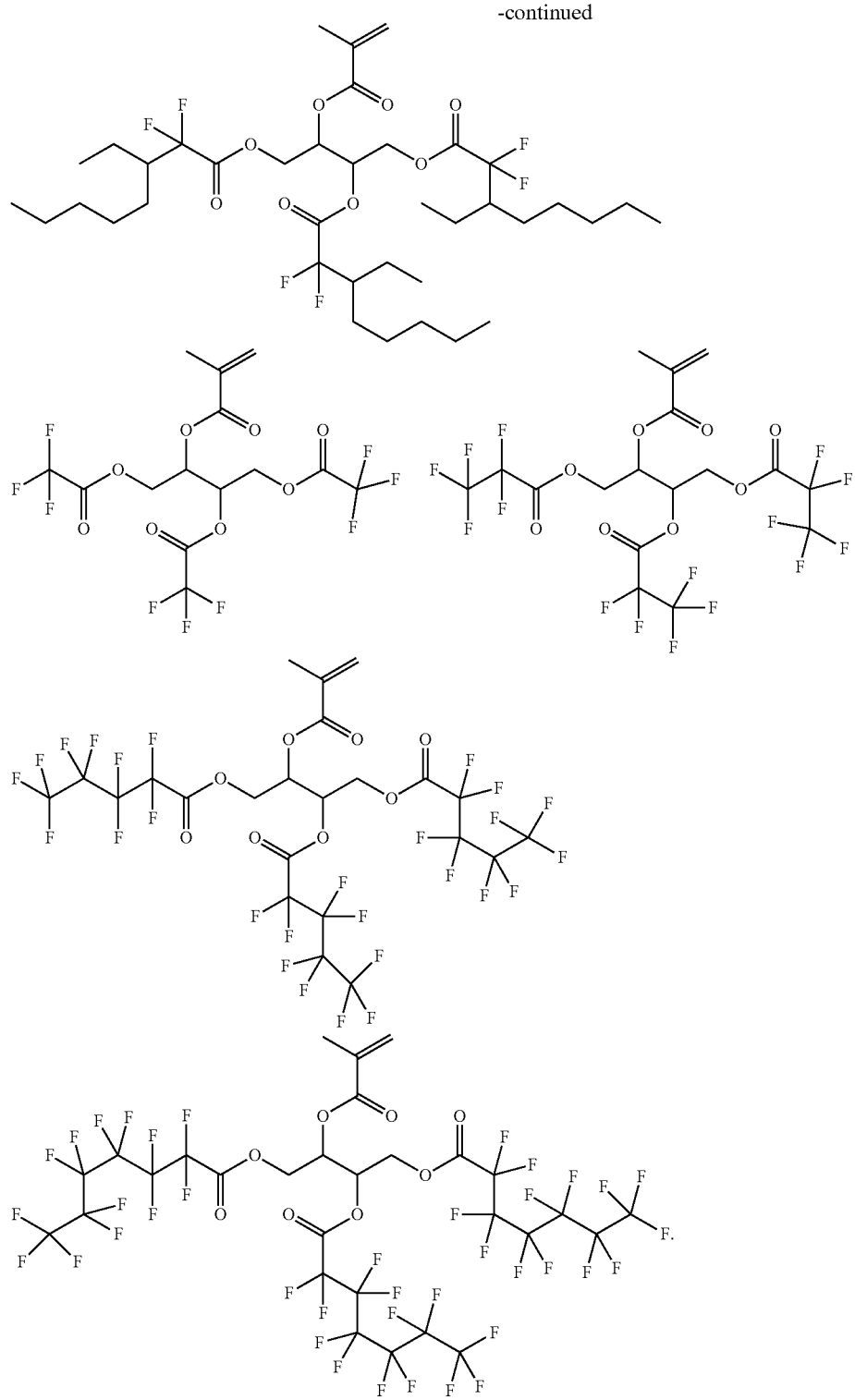
17. A photoresist composition comprising a photoactive component and a polymer of claim 15.
18. A photoresist composition comprising a photoactive component and a polymer of claim 17.
* * * * *